(12) United States Patent
Nakamura et al.

(10) Patent No.: US 10,799,101 B2
(45) Date of Patent: Oct. 13, 2020

(54) IMAGE PROCESSING APPARATUS, IMAGE PROCESSING METHOD, AND PROGRAM

(71) Applicant: SONY CORPORATION, Tokyo (JP)

(72) Inventors: Yukihiro Nakamura, Kanagawa (JP); Takami Mizukura, Kanagawa (JP); Tsuneo Hayashi, Tokyo (JP); Daisuke Kikuchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 208 days.

(21) Appl. No.: 15/329,313

(22) PCT Filed: Oct. 30, 2015

(86) PCT No.: PCT/JP2015/005487
§ 371 (c)(1),
(2) Date: Jan. 26, 2017

(87) PCT Pub. No.: WO2016/075890
PCT Pub. Date: May 19, 2016

(65) Prior Publication Data
US 2017/0209031 A1    Jul. 27, 2017

(30) Foreign Application Priority Data
Nov. 12, 2014   (JP) .................................. 2014-229368

(51) Int. Cl.
*A61B 1/06*    (2006.01)
*A61B 1/00*    (2006.01)
(Continued)

(52) U.S. Cl.
CPC ........ *A61B 1/0638* (2013.01); *A61B 1/00009* (2013.01); *A61B 1/00045* (2013.01);
(Continued)

(58) Field of Classification Search
CPC .............. G02B 21/365; G02B 23/2484; H04N 5/2256; H04N 2005/2255; A61B 1/04;
(Continued)

(56) References Cited

U.S. PATENT DOCUMENTS

| 2005/0065436 A1 | 3/2005 | Ho et al. |
| 2007/0299309 A1* | 12/2007 | Seibel .................. A61B 1/0008 600/117 |

(Continued)

FOREIGN PATENT DOCUMENTS

| CN | 102695446 A | 9/2012 |
| EP | 1 839 558 | 10/2007 |

(Continued)

OTHER PUBLICATIONS

Neil (Multispectral image alignment using a three channel endoscope in vivo during minimally invasive surgery—Received Jun. 18, 2012; rev. Sep. 7, 2012; accepted Sep. 11, 2012; published Sep. 14, 2012; Oct. 1, 2012 / vol. 3, No. 10 / Biomedical Optics (Year: 2012).*

(Continued)

*Primary Examiner* — Nasim N Nirjhar
(74) *Attorney, Agent, or Firm* — Xsensus LLP

(57) ABSTRACT

An image processing apparatus includes a special light image acquisition unit that acquires a special light image having information in a specific wavelength band, a generation unit that generates depth information at a predetermined position in a living body using the special light image, and a detection unit that detects a predetermined region using the depth information. The image processing apparatus further includes a normal light image acquisition unit that acquires a normal light image having information in a wavelength band of white light. The specific wavelength band is, for example, infrared light. The generation unit (Continued)

calculates a difference in a depth direction between the special light image and the normal light image to generate depth information at the predetermined position. The detection unit detects a position in which the depth information is a predetermined threshold or more as a bleeding point. The present technology is applicable to an endoscope.

22 Claims, 20 Drawing Sheets

(51) Int. Cl.
| | |
|---|---|
| A61B 5/00 | (2006.01) |
| A61B 5/02 | (2006.01) |
| A61B 1/04 | (2006.01) |
| G02B 21/36 | (2006.01) |
| G02B 23/24 | (2006.01) |
| H04N 5/225 | (2006.01) |

(52) U.S. Cl.
CPC .............. *A61B 1/04* (2013.01); *A61B 5/0086* (2013.01); *A61B 5/02007* (2013.01); *G02B 21/365* (2013.01); *G02B 23/2484* (2013.01); *H04N 5/2256* (2013.01); *A61B 5/0084* (2013.01); *A61B 5/02042* (2013.01); *H04N 2005/2255* (2013.01)

(58) Field of Classification Search
CPC .............. A61B 1/0638; A61B 1/00009; A61B 5/02007; A61B 1/00045; A61B 5/0086; A61B 5/02042; A61B 5/0084
See application file for complete search history.

(56) References Cited

U.S. PATENT DOCUMENTS

| | | | |
|---|---|---|---|
| 2008/0009669 A1 | 1/2008 | Ozawa et al. | |
| 2009/0214649 A1* | 8/2009 | Gazit | A61L 27/225<br>424/484 |
| 2010/0198009 A1* | 8/2010 | Farr | A61B 1/00103<br>600/109 |
| 2010/0331624 A1* | 12/2010 | Suzuki | A61B 1/0638<br>600/109 |
| 2012/0182409 A1* | 7/2012 | Moriyama | A61B 1/00006<br>348/65 |
| 2012/0259232 A1 | 10/2012 | Minetoma et al. | |
| 2012/0327205 A1 | 12/2012 | Takahashi | |
| 2014/0092390 A1* | 4/2014 | Watanabe | G01J 3/26<br>356/456 |
| 2015/0219552 A1* | 8/2015 | Kanamori | G01N 21/21<br>356/369 |
| 2016/0000307 A1* | 1/2016 | Akimoto | A61B 1/04<br>600/109 |
| 2018/0200004 A1* | 7/2018 | Carnes | A61B 34/30 |

FOREIGN PATENT DOCUMENTS

| | | |
|---|---|---|
| EP | 1 839 558 A1 | 10/2007 |
| EP | 2 505 121 | 10/2012 |
| EP | 2 505 121 A1 | 10/2012 |
| EP | 2 520 214 | 11/2012 |
| EP | 2 520 214 A1 | 11/2012 |
| JP | 2006-68113 A | 3/2006 |
| JP | 2007-229053 A | 9/2007 |
| JP | 2010-22464 A | 2/2010 |
| JP | 2010-537771 A | 12/2010 |
| JP | 2011-87906 A | 5/2011 |
| JP | 2011-135983 A | 7/2011 |
| JP | 2012-245157 A | 12/2012 |
| JP | 2013-150713 A | 8/2013 |
| JP | 2013-215471 A | 10/2013 |
| WO | WO 2008/035685 A | 3/2008 |
| WO | WO 2008/102803 A1 | 8/2008 |
| WO | WO 2012/035923 A1 | 3/2012 |
| WO | WO 2014/013950 A1 | 1/2014 |

OTHER PUBLICATIONS

Office Action dated Nov. 30, 2017 in corresponding Japanese Patent Application No. 2014-229368 (with English Translation), 10 pages.
International Search Report dated Aug. 2, 2016, in PCT/JP2015/005487 filed Oct. 30, 2015.
Office Action dated Jun. 7, 2018 in corresponding Japanese Patent Application No. 2014-229368 (with English Translation), 14 pages.
Combined Chinese Office Action and Search Report dated Jun. 1, 2018 in corresponding Chinese Patent Application No. 201580060121.8 (with English Translation), 15 pages.
Office Action dated Jan. 8, 2019 in European Patent Application No. 15 794 658.3, 6 pages.

\* cited by examiner

IMAGE PROCESSING APPARATUS, IMAGE PROCESSING METHOD, AND PROGRAM

TECHNICAL FIELD

The present technology relates to an image processing apparatus, an image processing method, and a program. Specifically, the present technology relates to an image processing apparatus, an image processing method, and a program suitably applicable to an apparatus such as an endoscope that captures an image of the inside of the body cavity of a subject to obtain information of the inside of the body cavity.

CROSS REFERENCE TO RELATED APPLICATIONS

This application claims the benefit of Japanese Priority Patent Application JP 2014-229368 filed on Nov. 12, 2014, the entire contents of which are incorporated herein by reference.

BACKGROUND ART

There has been widely used a frame sequential endoscope system that sequentially applies beams of light R1, G1, and B1 of three colors to a tissue inside the body cavity using a rotary filter and performs diagnosis using an image (normal light image) created from reflected light images of these light beams. Further, there has been proposed an endoscope system that sequentially applies two kinds of narrow band light beams G2 and B2 having characteristics different from the characteristics of the above three-color light beams to a tissue inside the body cavity and performs diagnosis using a narrow band light image created from reflected light images of these light beams (e.g., PTL 1).

When diagnosis is performed using an endoscope system that acquires a narrow band light image, for example, a lesion such as squamous cell carcinoma, which is difficult to visually recognize in a normal light image, is visualized as a brown region different from a normal part. Thus, it is easy to detect a lesion.

There has also been proposed an endoscope system that applies excitation light of a narrow band to a tissue inside the body cavity and performs diagnosis using a fluorescence image created by acquiring autofluorescence generated from the tissue by the excitation light or chemical fluorescence (e.g., PTL 2).

When diagnosis is performed using an endoscope system that acquires a fluorescence image, only a lesion such as a tumor emits fluorescence by using a fluorescence agent that has a property of specifically accumulating on a lesion such as a tumor, so that the lesion can be easily detected.

However, a narrow band light image and a fluorescence image (collectively referred to as special light images) typically have a color that is largely different from the color of a normal light image. Further, these special light images are extremely dark due to the lack of illumination light. Thus, it is difficult to perform diagnosis by using only a special light image. In view of this, in order to improve the diagnostic accuracy for a user, for example, a normal light image and a special light image may be simultaneously acquired and displayed. However, simultaneously displaying these images side by side causes a user to perform diagnosis while paying attention to a plurality of images all the time. This increases the load on the user. Further, a user may overlook a lesion by temporarily paying attention to a single image.

Therefore, PTL 3 has proposed that a first image corresponding to a wavelength range of white light and a second image corresponding to a specific wavelength range are acquired to determine the kind of a subject image within the second image and apply highlighting processing to the first image in accordance with the kind of the subject image to thereby prevent a lesion from being overlooked while reducing the load on a user.

CITATION LIST

Patent Literature

PTL 1: JP 2006-68113 A
PTL 2: JP 2007-229053 A
PTL 3: JP 2011-135983 A

SUMMARY OF INVENTION

Technical Problem

Methods in related art including PTLs 1 to 3 perform feature detection based on a feature amount obtained from a planar image by a 2D image. Thus, it is difficult to obtain information of the three-dimensional (3D) structure of a subject and the 3D positional relationship between objects, for example, blood vessels. Therefore, it may be difficult to perform kind determination and feature detection on a subject image.

The present technology has been made in view of such circumstances to enable information of a 3D structure and the positional relationship between objects to be easily acquired by using depth information.

Solution to Problem

A medical system according to an embodiment of the present technology includes: a medical imaging device, and an image processing apparatus for processing an image captured by the medical imaging device that includes circuitry configured to acquire a special light image from the image captured by the medical imaging device, the special light image having information limited to a specific wavelength band, generate depth information at a predetermined position of a patient using the special light image, and detect a structural relationship using the depth information.

An image processing method according to an embodiment of the present technology includes: acquiring a special light image, from the image captured by the medical imaging device, the special light image having information limited to a specific wavelength band, generating depth information at a predetermined position of a patient using the special light image, and detecting a structural relationship using the depth information.

A non-transitory computer readable medium having stored thereon a program that when executed by a computer causes the computer to execute processing. The processing according to an embodiment of the present technology includes: acquiring a special light image, from the image captured by the medical imaging device, the special light image having information limited to a specific wavelength band, generating depth information at a predetermined position of a patient using the special light image, and detecting a structural relationship using the depth information.

An image processing apparatus for processing an image captured by the medical imaging device according to an embodiment of the present technology includes: circuitry configured to acquire a special light image from the image captured by the medical imaging device, the special light image having information limited to a specific wavelength band, generate depth information at a predetermined position of a patient using the special light image, and detect a structural relationship using the depth information.

Advantageous Effect of Invention

An embodiment of the present technology enables information of a 3D structure and the positional relationship between objects to be easily acquired by using depth information.

The effects of the present technology are not necessarily limited to the effect described herein and may be any of the effects described in the present disclosure.

DESCRIPTION OF EMBODIMENTS

Hereinbelow, a mode for carrying out the present technology (hereinbelow, referred to as an embodiment) is described. The description is made in the following order.
1. Configuration of Image Processing Apparatus
2. Operation of Image Processing Apparatus
3. Application to Detection of Bleeding Position
4. Application to Detection of Transparent Membrane Thickness
5. Application to Detection of Mist
6. Application to Detection of Artery and Vein
7. Application to Detection of Overlapping State of Blood Vessels
8. Application to Detection of Tumor
9. Recording Medium <Configuration of Image Processing Apparatus>

Figure 1:
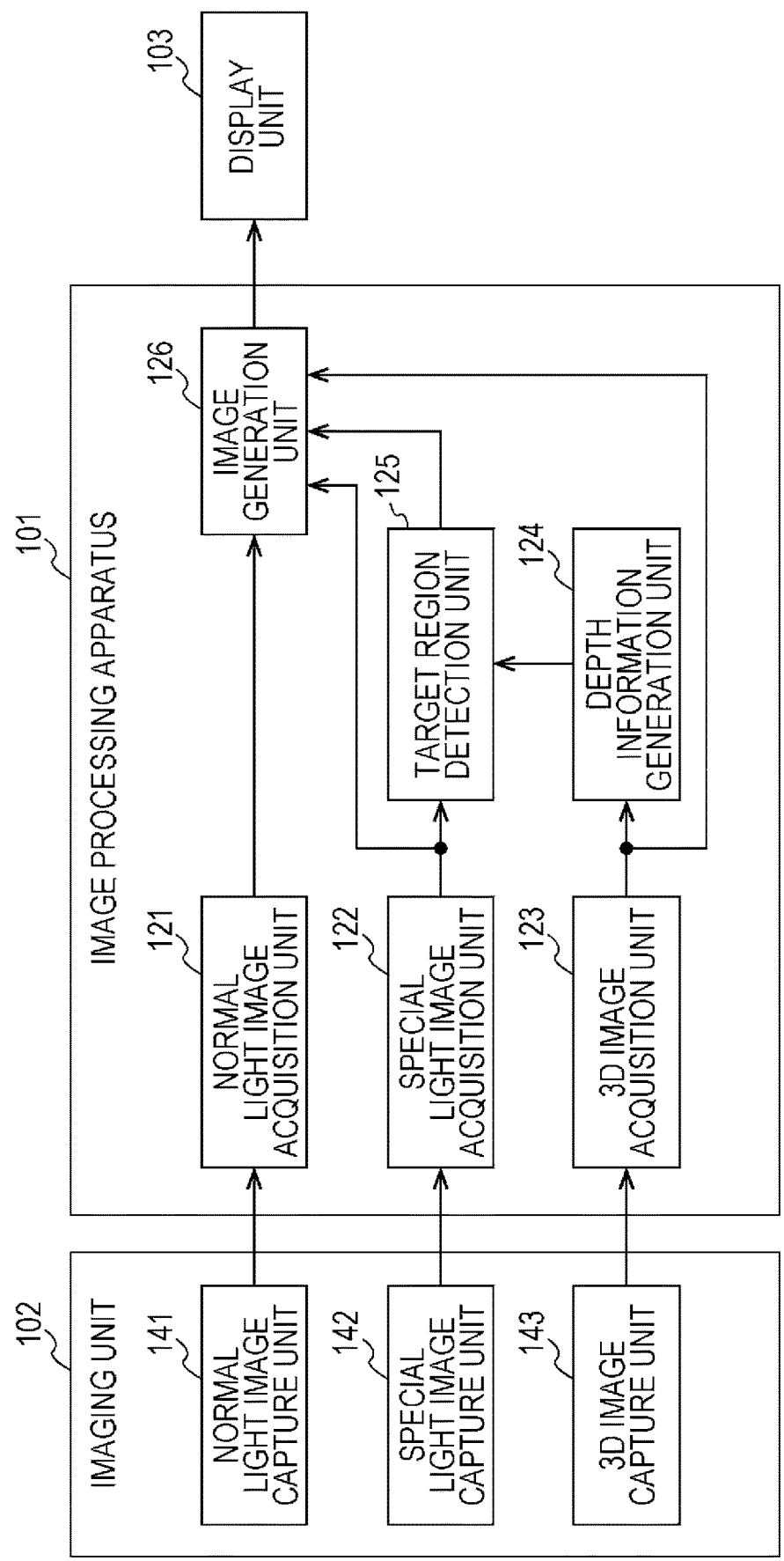
FIG. 1 is a diagram illustrating a configuration of an embodiment of an image processing apparatus to which the present technology is applied.

FIG. 1 is a diagram illustrating a configuration of an embodiment of an image processing system that includes an image processing apparatus to which the present technology is applied. An image processing apparatus 101 to which the present technology is applied is applicable to an apparatus that constitutes a part of an endoscope system or a microscope system and applicable to an apparatus that processes an image obtained by imaging the inside of the body cavity of a subject.

The image processing apparatus 101 processes an image captured by an imaging unit 102 and outputs the processed image to a display unit 103. The display unit 103 includes a display and displays an image processed by the image processing apparatus 101.

FIG. 1 illustrates the image processing apparatus 101, the imaging unit 102, and the display unit 103 as different bodies. Alternatively, the image processing apparatus 101 may include a part of the imaging unit 102 or the entire imaging unit 102, or may include a part of the display unit 103 or the entire display unit 103.

The image processing apparatus 101 includes a normal light image acquisition unit 121, a special light image acquisition unit 122, a 3D image acquisition unit 123, a depth information generation unit 124, a target region detection unit 125, and an image generation unit 126.

The imaging unit 102 includes a normal light image capture unit 141, a special light image capture unit 142, and a 3D image capture unit 143.

The image processing system illustrated in FIG. 1 is applicable to an endoscope system as described above. When the image processing system illustrated in FIG. 1 is applied to an endoscope system, the imaging unit 102 is formed in a shape insertable into the body cavity of a subject.

For example, the imaging unit 102 is formed in an elongated and bendable shape so as to be insertable into the body cavity. The imaging unit 102 has a detachable structure so that different imaging units are used depending on regions to be observed. In the endoscopic field, the imaging unit 102 is typically called a scope. Concrete examples of a scope to be used include an upper digestive organ scope and a lower digestive organ scope.

Although not illustrated, the imaging unit 102 includes a light source unit for the purpose of imaging a dark part. Normal light is used as a light source, and the normal light image capture unit 141 captures an image of a part irradiated with the normal light. Special light is used as a light source, and the special light image capture unit 142 captures an image of a part irradiated with the special light. Alternatively, the special light image capture unit 142 applies normal light and captures an image of light that is emitted from a part irradiated with the normal light and passes through a color filter having a specific color.

The 3D image capture unit 143 captures an image of a part irradiated with at least either normal light or special light. The captured image is a stereoscopic image (3D image).

Figure 2:
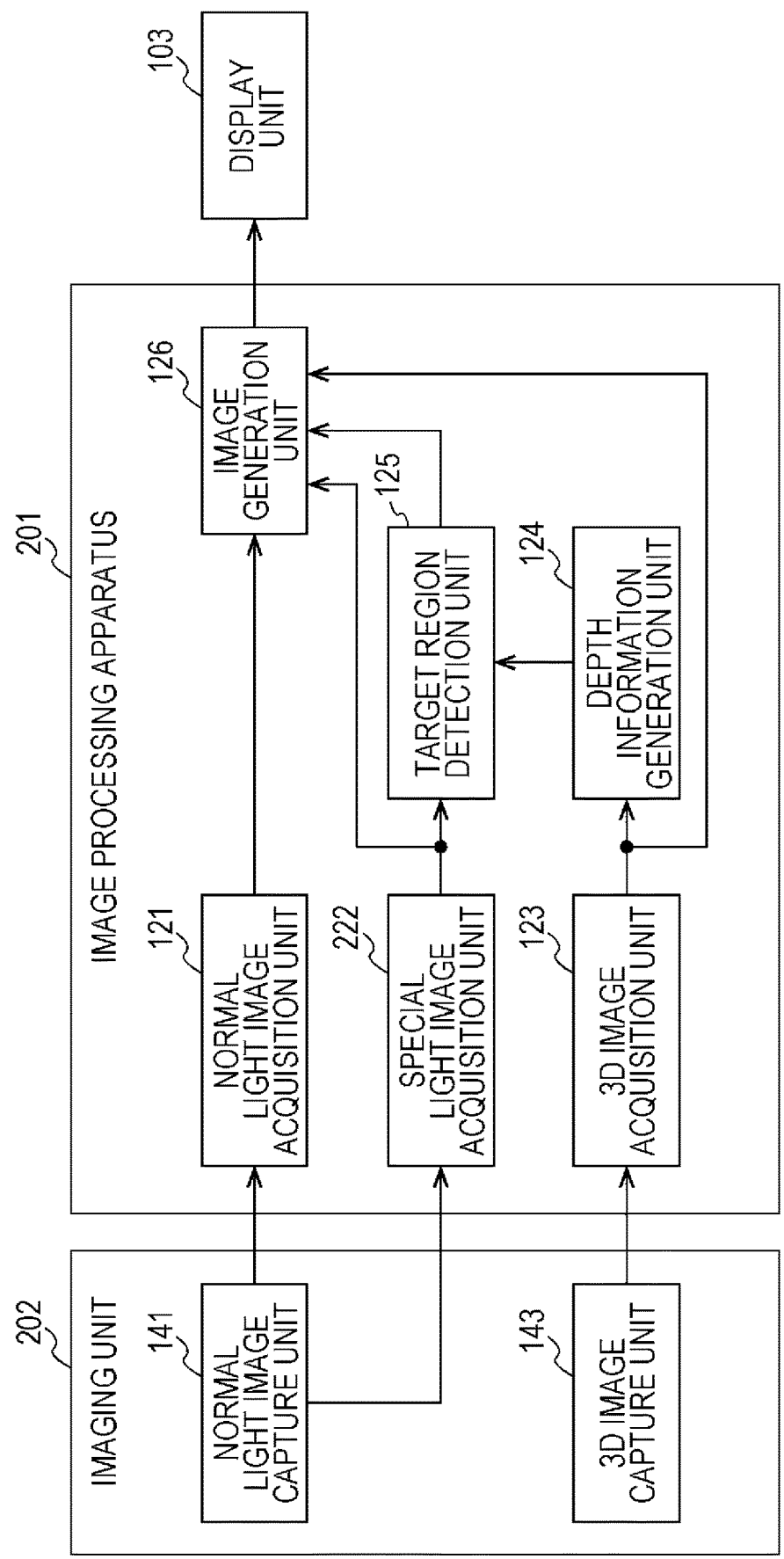
FIG. 2 is a diagram illustrating another configuration of the embodiment of the image processing apparatus to which the present technology is applied.

As illustrated in FIG. 2 and described below, a special light image may be generated from an image captured by the normal light image capture unit 141 without providing the special light image capture unit 142 illustrated in FIG. 1. Infrared light (IR) or narrow band wavelength light is used as the special light.

FIG. 1 illustrates, as an example, the 3D image capture unit 143 which is provided separately from the normal light image capture unit 141 and the special light image capture unit 142. Alternatively, as described below with reference to FIG. 3, the normal light image capture unit 141 and the special light image capture unit 142 may capture 3D images, respectively.

The normal light image acquisition unit 121 of the image processing apparatus 101 acquires image data of an image captured by the normal light image capture unit 141. The normal light image acquisition unit 121 is provided with an analog-digital converter (AD converter, not illustrated). The normal light image acquisition unit 121 may convert an analog image signal to a digital image signal to acquire image data or may acquire digital image data from the normal light image capture unit 141.

Similarly, the special light image acquisition unit 122 of the image processing apparatus 101 acquires image data of an image captured by the special light image capture unit 142. In the following description, an image acquired by the special light image acquisition unit 122 is referred to as a special light image. An image acquired by the normal light image acquisition unit 121 is referred to as a normal light image. An image acquired by the 3D image acquisition unit 123 is referred to as a 3D image.

The depth information generation unit 124 of the image processing apparatus 101 generates depth information from a 3D image acquired by the 3D image acquisition unit 123. The target region detection unit 125 detects a predetermined region using depth information supplied from the depth information generation unit 124 and a special light image supplied from the special light image acquisition unit 122.

For example, the target region detection unit 125 generates information such as the thickness of a predetermined membrane and the positional relationship between blood vessels, for example, between a front blood vessel and a rear blood vessel. Concrete examples of how to use the depth information and information to be generated are described below.

The image generation unit 126 generates an image to be provided to a user using a normal light image supplied from the normal light image acquisition unit 121, a special light image supplied from the special light image acquisition unit 122, a 3D image supplied from the 3D image acquisition unit 123, and information about a target region detected by the target region detection unit 125.

For example, an image in which information about a target region, for example, a numerical value of the membrane thickness is superimposed on a normal light image is generated. Displaying visually recognizable information, for example, a numerical value of the membrane thickness on an image, for example, a normal light image, a special light image, or a 3D light image in this manner enables a user to obtain information that is difficult to obtain merely by looking at the normal light image, the special light image, or the 3D light image. Thus, the usability is obviously improved.

FIG. 2 is a diagram illustrating another configuration of the embodiment of the image processing system which includes the image processing apparatus to which the present technology is applied. A part of the image processing system illustrated in FIG. 2, the part having a configuration similar to that of the image processing system illustrated in FIG. 1 is designated by the same reference sign. Hereinbelow, description of the similar part is appropriately omitted, and a different part is described.

The image processing system illustrated in FIG. 2 also includes an image processing apparatus 201, an imaging unit 202, and a display unit 103. The image processing apparatus 201 has the same configuration as the image processing apparatus 101 illustrated in FIG. 1 excepting that a special light image acquisition unit 222 acquires a normal light image from a normal light image capture unit 141 of the imaging unit 202.

The imaging unit 202 includes the normal light image capture unit 141 and a 3D image capture unit 143. The imaging unit 202 illustrated in FIG. 2 differs from the imaging unit 102 illustrated in FIG. 1 in that no special light image capture unit 142 is provided.

The special light image acquisition unit 222 of the image processing apparatus 201 receives the supply of a normal light image from the normal light image capture unit 141. Although, here, the special light image acquisition unit 222 is described to receive the supply of a normal light image from the normal light image capture unit 141, the special light image acquisition unit 222 may receive the supply of a normal light image acquired by the normal light image acquisition unit 121 from the normal light image capture unit 141.

The special light image acquisition unit 222 has a function of generating a special light image from a normal light image. The special light image is an image captured with light in a predetermined band, for example, an image obtained by imaging a part that reacts to blue light when irradiated with the blue light. The special light image acquisition unit 222 extracts a blue component image from a normal light image to generate a special light image.

The image processing system illustrated in FIG. 2 acquires a special light image from a normal light image in this manner.

Figure 3:
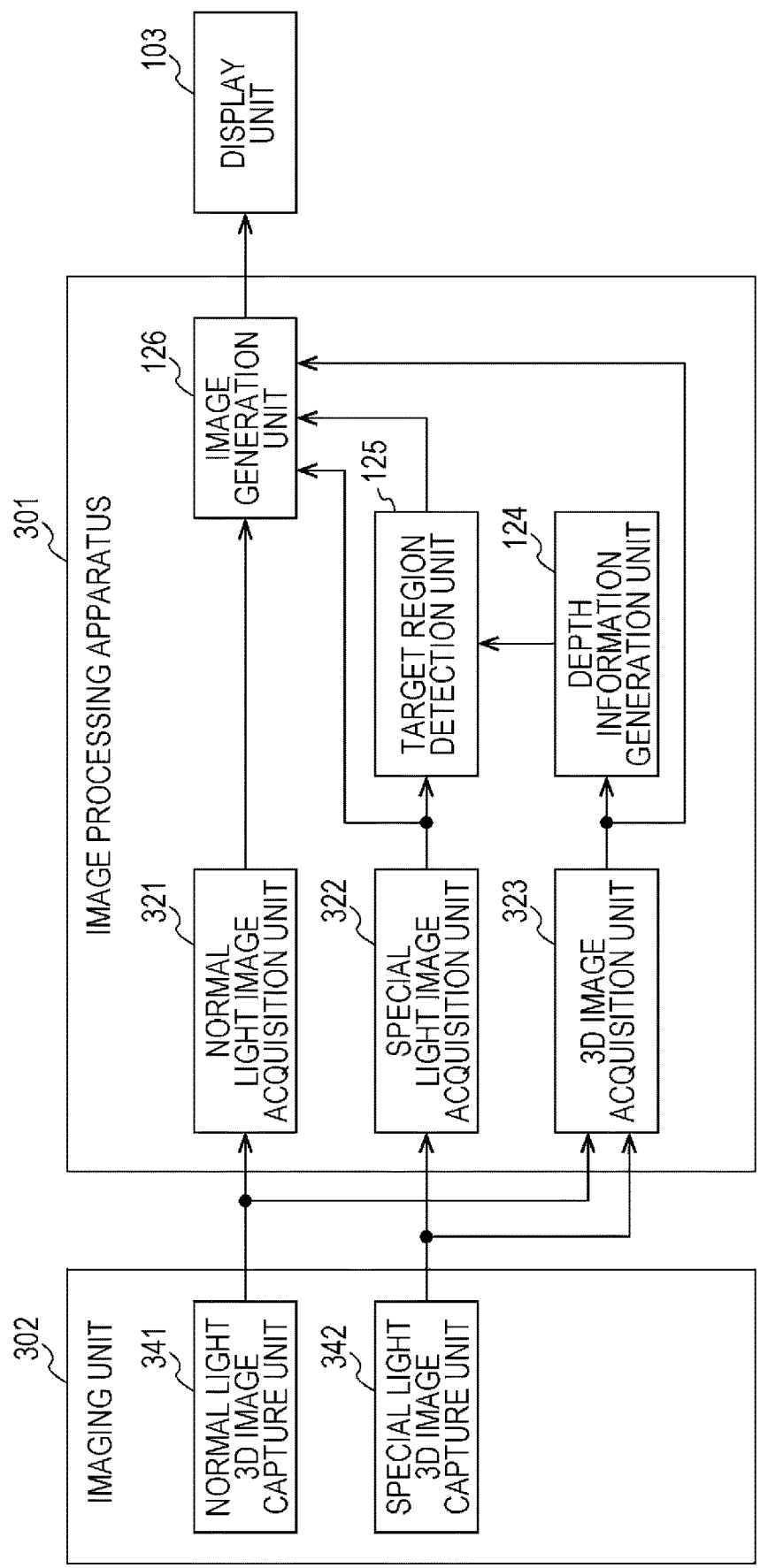
FIG. 3 is a diagram illustrating still another configuration of the embodiment of the image processing apparatus to which the present technology is applied.

FIG. 3 is a diagram illustrating still another configuration of the embodiment of the image processing system which includes the image processing apparatus to which the present technology is applied. A part of the image processing system illustrated in FIG. 3, the part having a configuration similar to that of the image processing system illustrated in FIG. 1 is designated by the same reference sign. Hereinbelow, description of the similar part is appropriately omitted, and a different part is described.

An imaging unit 302 of the image processing system illustrated in FIG. 3 includes a normal light 3D image capture unit 341 and a special light 3D image capture unit 342. The normal light 3D image capture unit 341 captures a normal light 3D image obtained under normal light. The special light 3D image capture unit 342 captures a special light 3D image obtained under special light.

A normal light image acquisition unit 321 of an image processing apparatus 301 acquires a normal light 3D image captured by the normal light 3D image capture unit 341. The normal light image acquisition unit 321 may generate a 2D image from the acquired normal light 3D image and supply the generated normal light 2D image to an image generation unit 126, or may supply the acquired normal light 3D image to the image generation unit 126 to provide a user with the normal light 3D image as it is.

A special light image acquisition unit 322 of the image processing apparatus 301 acquires a special light 3D image captured by the special light 3D image capture unit 342. The special light image acquisition unit 322 may generate a 2D image from the acquired special light 3D image and supply the generated special light 2D image to the image generation unit 126, or may supply the acquired special light 3D image to the image generation unit 126 to provide a user with the special light 3D image as it is.

A 3D image acquisition unit 323 acquires a normal light 3D image from the normal light 3D image capture unit 341 and a special light 3D image from the special light 3D image capture unit 342. A depth information generation unit 124 generates depth information from the acquired normal light 3D image and the acquired special light 3D image depending on what is to be detected by a target region detection unit 125.

In each of the image processing apparatuses illustrated in FIGS. 1 to 3, a user may select which one is to be displayed on the display unit 103 among the normal light image, the special light image, and the 3D image. Although not illustrated, the image processing apparatus is also provided with an operation unit which receives such an instruction from a user.

The configurations of the image processing apparatuses described herein are merely examples, and indicate no limitation. For example, in the image processing apparatus 301 illustrated in FIG. 3, a special light image may be generated from a normal light image as with the image processing apparatus 201 illustrated in FIG. 2. In such a configuration, a normal light 3D image may be supplied from the normal light 3D image capture unit 341 of the imaging unit 302 to the special light image acquisition unit 322 of the image processing apparatus 301.

That is, as described above, a special light image having information in a specific wavelength band may be acquired by performing imaging using light in the specific wavelength band or may be acquired by extracting information in the specific wavelength band from a normal light image captured using light in a wavelength band of normal light (white light).

Further, a 3D image may be acquired by performing stereoscopic image capturing or may be acquired by acquiring a 2D image and then converting the 2D image to the 3D image.

Next, processing executed in the image processing apparatuses illustrated in FIGS. 1 to 3 is described. First, the processing of the image processing apparatuses illustrated in FIGS. 1 to 3 is described in outline with reference to a flowchart of FIG. 4. Then, description with concrete examples of a region to be detected is made.

<Operation of Image Processing Apparatus>

Figure 4:
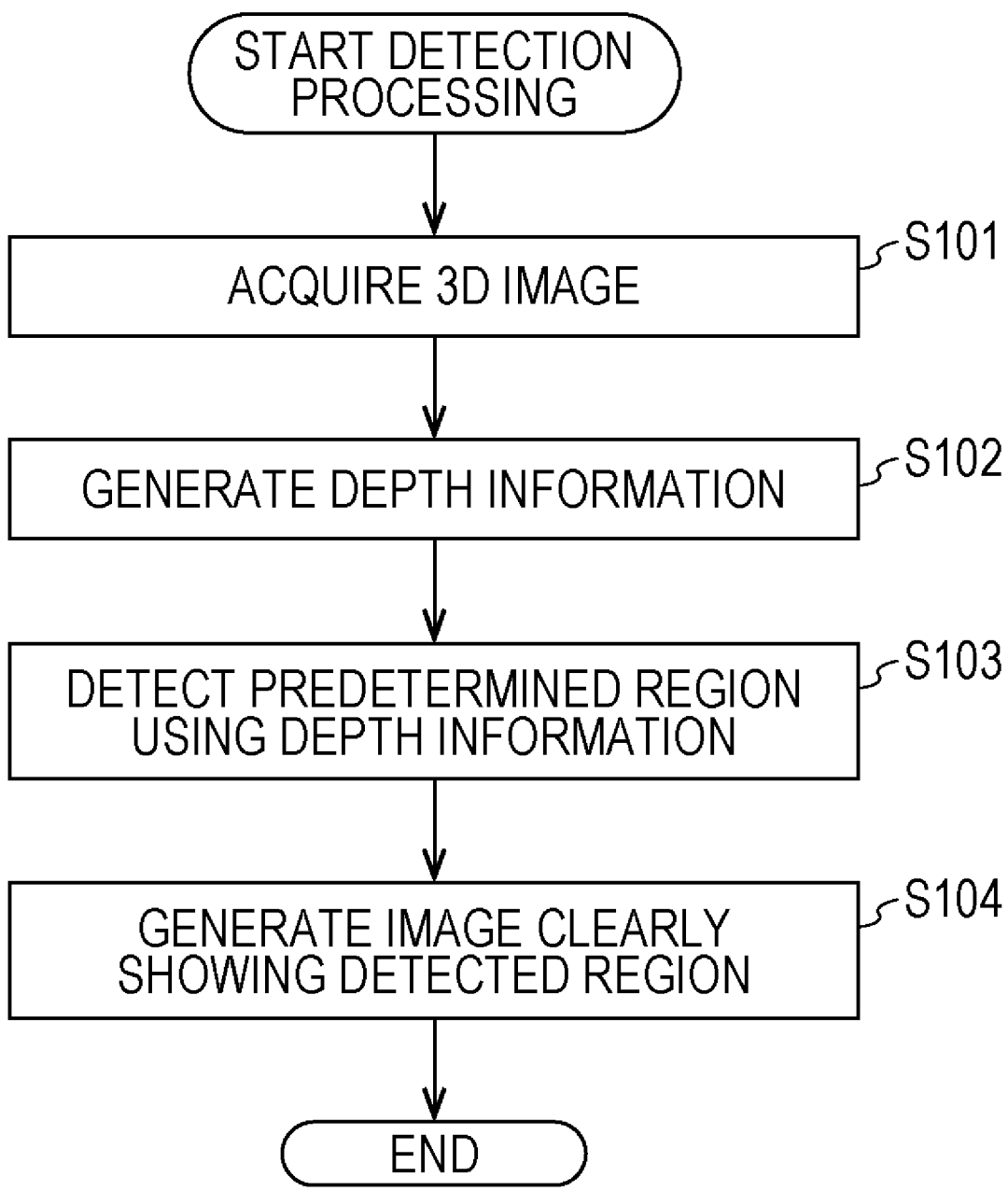
FIG. 4 is a flowchart for describing processing of the image processing apparatus.

The processing of the image processing apparatus is described in outline with reference to the flowchart of FIG. 4. Although, here, the image processing apparatus 301 illustrated in FIG. 3 is described as an example, processing is basically performed in a similar manner also in the image processing apparatus 101 illustrated in FIG. 1 and the image processing apparatus 201 illustrated in FIG. 2.

In step S101, the 3D image acquisition unit 323 acquires a normal light 3D image from the normal light 3D image capture unit 341 and acquires a special light 3D image from the special light 3D image capture unit 342. In step S102, the depth information generation unit 124 generates depth information from the 3D images acquired by the 3D image acquisition unit 323. The depth information is generated using coordinates of the 3D images at a predetermined position, in particular, coordinates in the depth direction.

In step S103, the target region detection unit 125 detects a predetermined region, for example, a blood vessel or a tumor using the depth information and a special light image acquired by the special light image acquisition unit 322. In step S104, the image generation unit 126 generates an image that clearly shows the detected region to a user and outputs the generated image to the display unit 103.

In this manner, the image processing apparatus to which the present technology is applied is capable of performing more detailed detection of a target region in more detail by also using depth information obtained from 3D images. Further, it is also possible to present the depth information to a user. Thus, for example, positional information of a blood vessel can be presented in more detail.

<Application to Detection of Bleeding Position>

Next, the processing of the image processing apparatus 301 is further described with a concrete example in which a bleeding region is detected as a region to be detected. First, a principle of detecting a bleeding position is described with reference to FIG. 5.

Figure 5:
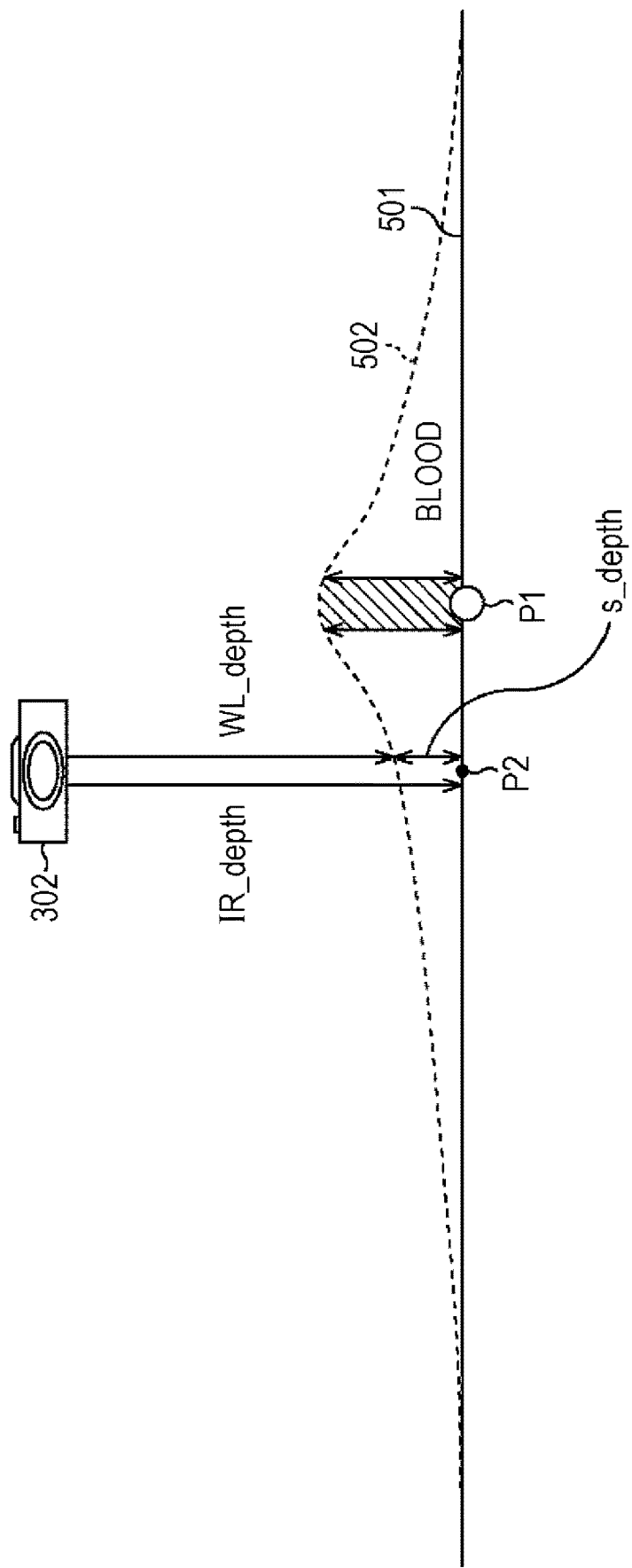
FIG. 5 is a diagram for describing a principle of detecting a bleeding position.

In FIG. 5, a flesh surface 501 is illustrated on the lower side. A puddle of blood is formed on the flesh surface 501 by bleeding. The buddle of blood has a blood surface 502. It is conceivable that a bleeding part of the puddle of blood rises higher than the other part of the puddle of blood. It is conceivable that, if the flesh surface 501 is flat, as illustrated in FIG. 5, a bleeding point P1 rises higher than the other part.

In practice, the flesh surface 501 may not be flat, but may be uneven. However, the difference between the flesh surface 501 and the blood surface 502, that is, the thickness of the puddle of blood is thick at the bleeding point P1. Thus, a 3D image of the flesh surface 501 and a 3D image of the blood surface 502 are acquired. Then, the difference between the 3D image of the flesh surface 501 and the 3D image of the blood surface 502 is calculated to measure the thickness of the puddle of blood at each position. When the thickness at a position is equal to or larger than a certain thickness, the position can be detected to be a bleeding point.

When infrared light (IR) is used as light during image capturing in imaging of the flesh surface 501 and the blood surface 502, the infrared light passes through the blood surface 502 and reaches the flesh surface 501. A 3D image of the flesh surface 501 is acquired by performing stereoscopic image capturing using infrared light by using such a characteristic.

On the other hand, when white light is used as light during image capturing, the white light is reflected by the blood surface 502 to return without passing through the blood surface 502. A 3D image of the blood surface 502 is acquired by performing stereoscopic image capturing using white light by using such a characteristic.

The normal light 3D image capture unit 341 of the imaging unit 302 (FIG. 3) performs image capturing using white light to acquire a 3D image of the blood surface 502. The special light 3D image capture unit 342 performs image capturing using infrared light to acquire a 3D image of the flesh surface 501. The difference between the two images is calculated to obtain thickness information of the puddle of blood at each point.

Referring to FIG. 5, at a point P2, a depth to the flesh surface 501 imaged using infrared light (IR) is denoted by depth IR_depth and a depth to the blood surface 502 imaged using white light (WL) is denoted by depth WL_depth. In this case, thickness s_depth of the puddle of blood at the point P2 can be represented by the following Equation 1.

$$\text{thickness } s\_depth = \text{depth IR}\_depth - \text{depth WL}\_depth$$

When the depth WL_depth obtained by such an arithmetic operation is greater than a predetermined threshold, the thickness of blood is large. Thus, such a position can be detected as a bleeding position. In this manner, a position having a depth WL_depth greater than the threshold is determined to be a bleeding position. Thus, it is possible to cope with a case in which there is a plurality of bleeding positions.

For example, when a position having the largest measured value is determined to be a bleeding position, only one position can be detected. On the other hand, since a position having a measured value equal to or greater than the threshold is determined to be a bleeding position, even when there is a plurality of bleeding positions, each of the positions can be determined to be a bleeding position.

Figure 6:
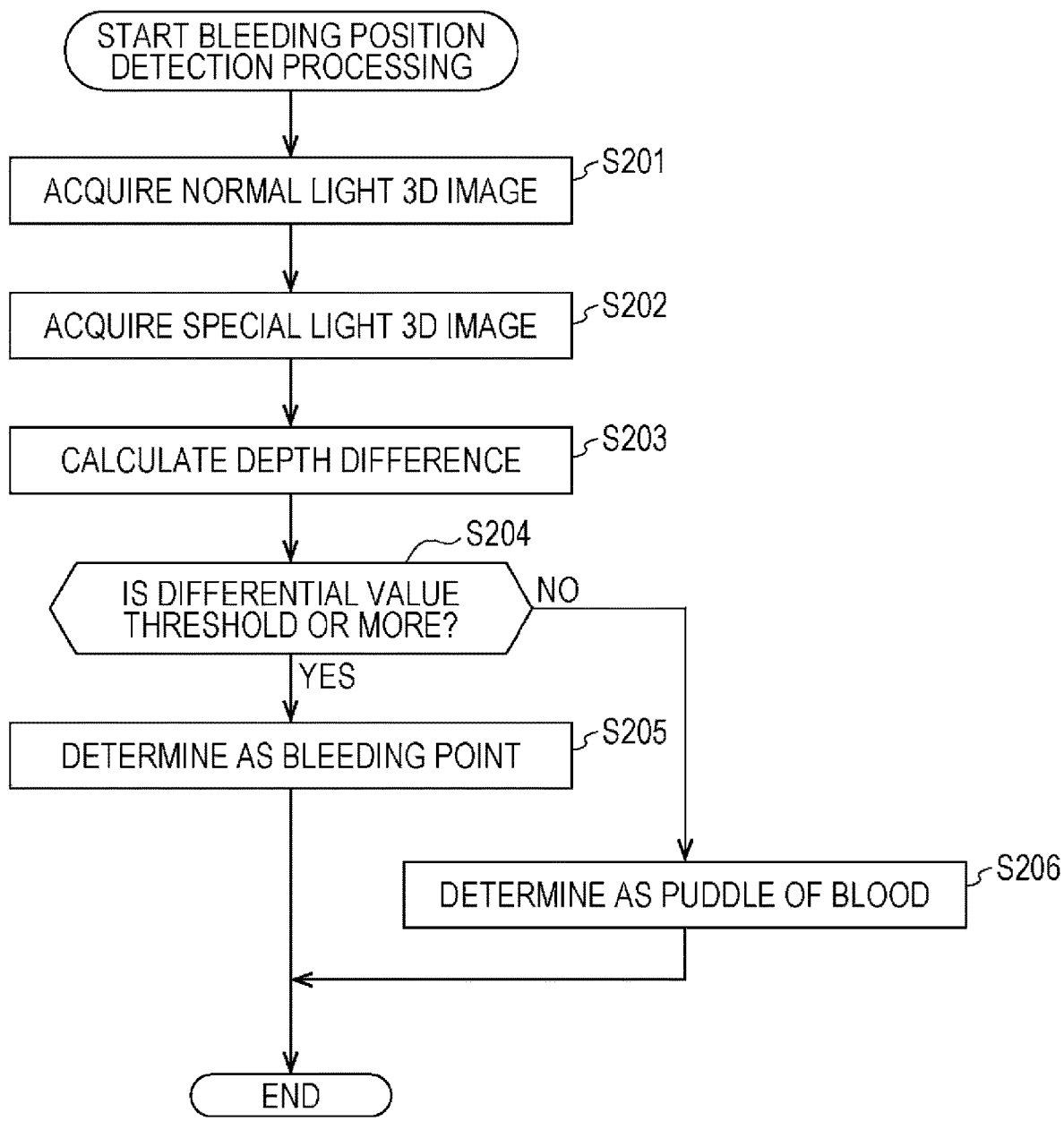
FIG. 6 is a flowchart for describing processing of the image processing apparatus when a bleeding position is detected.

An operation of the image processing apparatus 301 (FIG. 3) which performs such processing is described with reference to a flowchart of FIG. 6.

In step S201, a normal light 3D image is acquired. In this case, the normal light 3D image capture unit 341 of the imaging unit 302 performs imaging with white light to acquire the normal light 3D image, and the acquired normal light 3D image is supplied to the 3D image acquisition unit 323.

In step S202, a special light 3D image is acquired. In this case, the special light 3D image capture unit 342 of the imaging unit 302 performs imaging with infrared light to acquire the special light 3D image, and the acquired special light 3D image is supplied to the 3D image acquisition unit 323.

In step S203, the depth information generation unit 124 calculates a depth difference. The depth difference is calculated by performing the arithmetic operation of the above Equation 1 using coordinates in the depth direction of the 3D images. The arithmetic operation may be executed for all points (pixels) within the acquired image or an area that is determined to have a puddle of blood to generate thickness information of blood, or the acquired image may be divided into areas each having a predetermined size and the arithmetic operation may be executed for each of the areas to generate thickness information of blood.

In step S204, it is determined whether the differential value calculated in step S203 is equal to or greater than the threshold. The determination may be made by the depth information generation unit 124 and the determined result may be supplied to the target region detection unit 125. Alternatively, the target region detection unit 125 may receive the supply of depth information (differential value) generated by the depth information generation unit 124 to make the determination.

When the differential value is determined to be equal to or greater than the threshold in step S204, the processing proceeds to step S205. In step S205, a current processing point at this point of time is set as a bleeding point. The point set as the bleeding point is displayed in a manner to be uniquely distinguishable from the other part of the puddle of blood within an image to be provided to a user, for example, the bleeding point is displayed with a predetermined mark, or text that indicates being the bleeding point is displayed. Such display may be superimposed on a normal light image or a special light image. Further, the image to be superimposed may be a 3D image.

On the other hand, when the differential value is determined to be less than the threshold in step S204, the processing proceeds to step S206. In step S206, a current processing point at this point of time is set as a part of the puddle of blood other than the bleeding point.

In this manner, it is possible to obtain a differential value from two 3D images and detect a bleeding point from the obtained differential value. Information about the detected bleeding point is presented to a user. Thus, a user can recognize the bleeding point, which is difficult to recognize merely by looking at the captured image, by browsing the information.

<Application to Detection of Transparent Membrane Thickness>

Next, the processing of the image processing apparatus 301 is further described with a concrete example in which a transparent membrane is detected as a region to be detected. First, a principle of detecting a transparent membrane is described with reference to FIG. 7.

Figure 7:
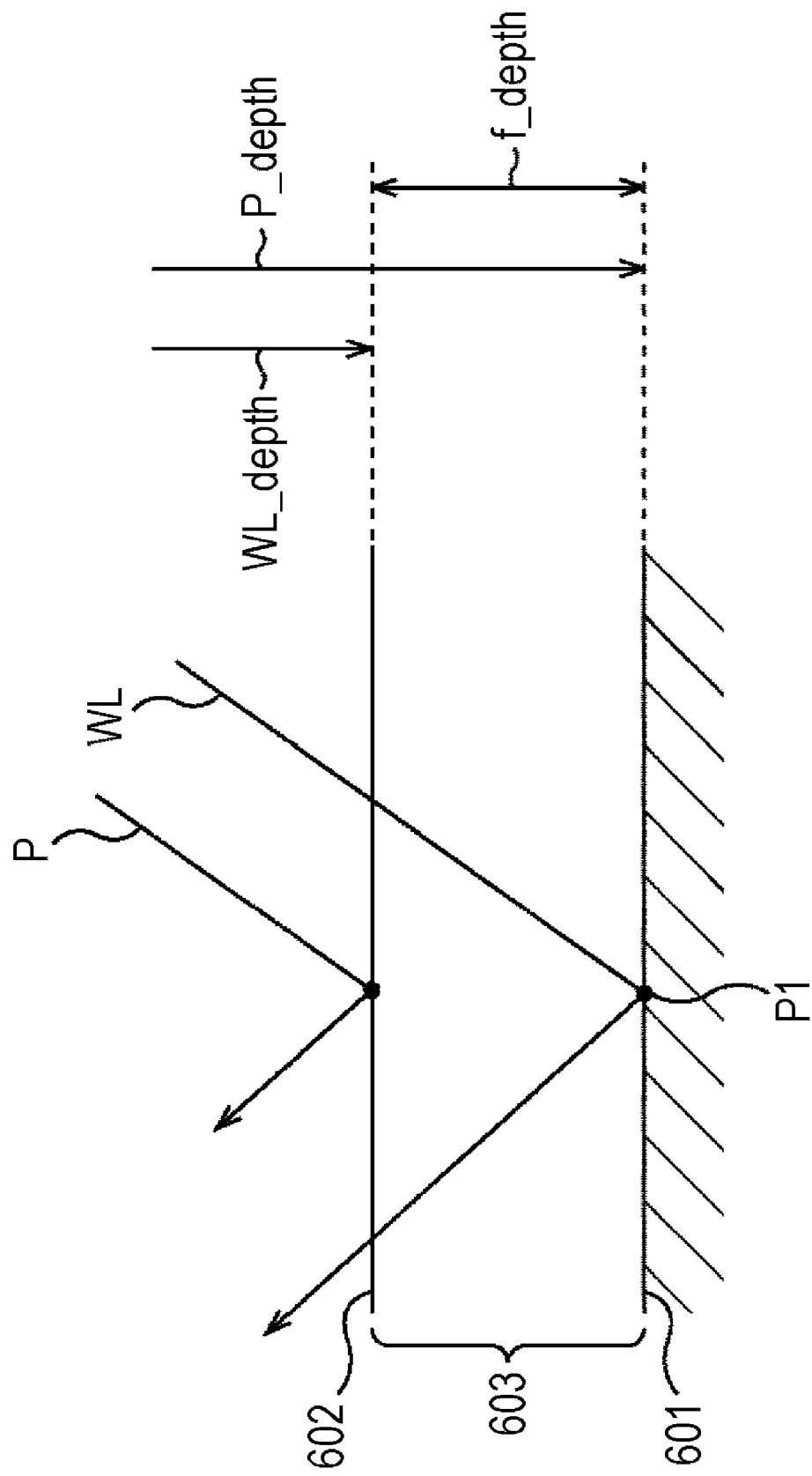
FIG. 7 is a diagram for describing a principle of detecting a transparent membrane.

In FIG. 7, a flesh surface 601 is illustrated on the lower side. A transparent membrane 603 having a predetermined thickness is located on the flesh surface 601. The transparent membrane 603 has a transparent membrane surface 602. It is difficult to capture an image of a transparent membrane with normal light (white light). Thus, it is difficult for a user to determine whether the transparent membrane is present in an image captured with white light.

However, it may be necessary to cut a transparent membrane to get the flesh surface 601. In such a case, presenting the thickness of the transparent membrane to a user makes it easy to know to what extent the transparent membrane should be cut. Accordingly, it is possible to improve the usability of apparatuses such as endoscopes and microscopes to which the image processing apparatus 301 is applied.

An image of the transparent membrane surface 602 can be captured by polarization image capturing. As illustrated in FIG. 7, polarized light P is reflected by the transparent membrane surface 602. Thus, the transparent membrane surface 602 can be imaged by imaging the reflected light. The flesh surface 601 can be imaged by imaging using white light (WL).

The normal light 3D image capture unit 341 of the imaging unit 302 (FIG. 3) performs stereoscopic image capturing using white light to acquire a 3D image of the flesh surface 601. The special light 3D image capture unit 342 performs stereoscopic image capturing using polarized light to acquire a 3D image of the transparent membrane surface 602. The difference between the two images is calculated to obtain thickness information of the transparent membrane 603 at each point.

Referring to FIG. 7, at a point P1, a depth to the flesh surface 601 imaged using white light (WL) is denoted by depth WL_depth and a depth to the transparent membrane surface 602 imaged using polarized light (P) is denoted by depth P_depth. In this case, membrane thickness f_depth of the transparent membrane 603 at the point P1 can be represented by the following Equation 2.

$$\text{membrane thickness } f\_depth = \text{depth WL}\_depth - \text{depth } P\_depth$$

Figure 8:
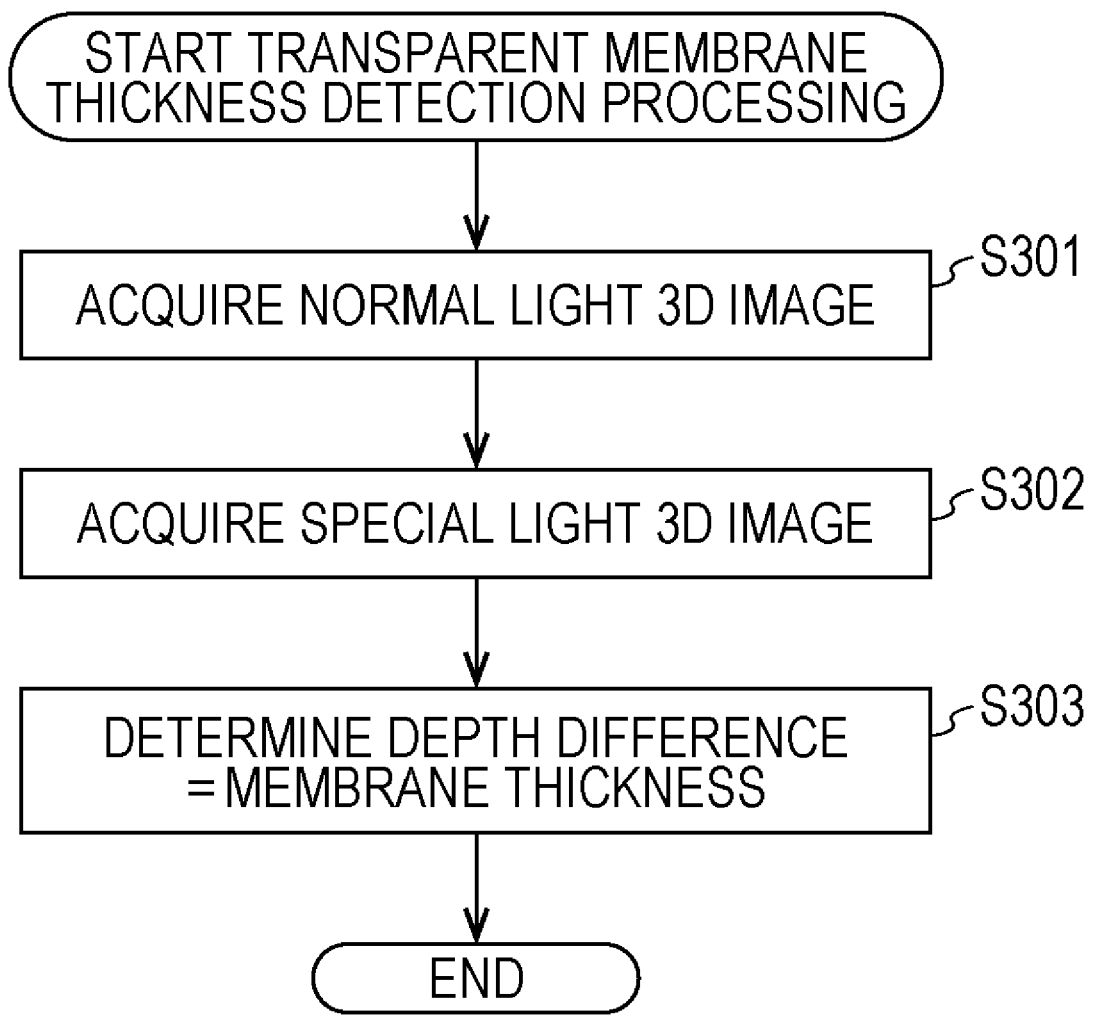
FIG. 8 is a flowchart for describing processing of the image processing apparatus when a transparent membrane is detected.

The membrane thickness f_depth obtained by such an arithmetic operation is defined as the thickness of the transparent membrane. An operation of the image processing apparatus 301 (FIG. 3) which performs such processing is described with reference to a flowchart of FIG. 8.

In step S301, a normal light 3D image is acquired. In this case, the normal light 3D image capture unit 341 of the imaging unit 302 performs stereoscopic imaging with white light to acquire the normal light 3D image, and the acquired normal light 3D image is supplied to the 3D image acquisition unit 323.

In step S302, a special light 3D image is acquired. In this case, the special light 3D image capture unit 342 of the imaging unit 302 performs polarization stereoscopic imaging to acquire the special light 3D image, and the acquired special light 3D image is supplied to the 3D image acquisition unit 323.

In step S303, the depth information generation unit 124 calculates a depth difference. The depth difference is calculated by performing the arithmetic operation of the above Equation 2 using coordinates in the depth direction of the 3D images. The differential value calculated in step S303 is set as the membrane thickness of the transparent membrane 603.

In this manner, the membrane thickness of the transparent membrane is detected. As the result of the arithmetic operation of Equation 2, when the differential value is zero or equal to or less than a predetermined threshold, it can be determined that there is no transparent membrane. That is, determining whether the differential value is equal to or greater than a predetermined threshold also enables the presence/absence of the transparent membrane 603 to be detected.

The membrane thickness of the transparent membrane detected in this manner is displayed as a numerical value or color information such as gradation within an image to be provided to a user. The display enables a user to recognize the presence/absence of the transparent membrane and the thickness of the transparent membrane at a glance. Such display may be superimposed on a normal light image or a special light image. Further, the image to be superimposed may be a 3D image.

For example, a numerical value of the membrane thickness may be displayed at a preset position, for example, a central part of a screen or the position of lattice points at a certain interval. Alternatively, display may be performed in such a manner that the color is changed corresponding to the membrane thickness and superimposed on a normal light image. Alternatively, a numerical value of the membrane thickness may be displayed at a position instructed by a user by operating an operation unit such as a pointer and a mouse.

In this manner, it is possible to obtain a differential value from two 3D images and detect a transparent membrane and the membrane thickness of the transparent membrane from the obtained differential value. Information about the detected transparent membrane is presented to a user. Thus, a user can recognize the transparent membrane, which is difficult to recognize merely by looking at the captured normal light image, by browsing the information. Since the membrane thickness of the transparent membrane can be recognized, a sense of putting a scalpel is easily got. This prevents flesh tissues from being erroneously damaged.

<Application to Detection of Mist>

Next, the processing of the image processing apparatus 301 is further described with a concrete example in which a mist is detected as a region to be detected. First, a principle of detecting a mist is described with reference to FIG. 9.

Figure 9:
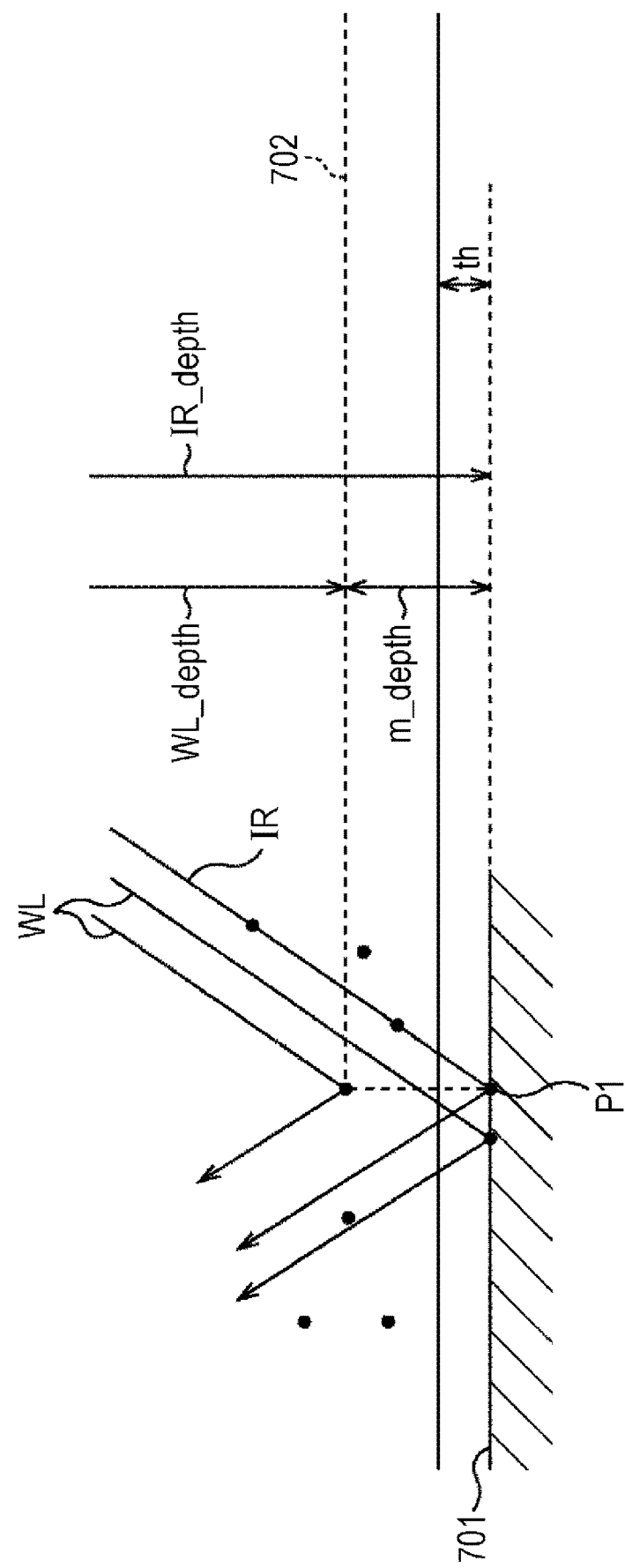
FIG. 9 is a diagram for describing a principle of detecting a mist.

In FIG. 9, a flesh surface 701 is illustrated on the lower side. A mist 703 having a predetermined thickness is located on the flesh surface 701. The mist 703 has a mist surface 702. When imaging is performed with normal light (white light), a mist component is reflected and imaged as a white point. A shine or glare caused by the structure of the flesh surface 701 may also be recognized as a white point. It is difficult to distinguish the mist and the shine in an image captured with normal light.

An image of the flesh surface 701 can be captured by infrared light image capturing. As illustrated in FIG. 9, infrared light IR passes through the mist surface 702 and is then reflected by the flesh surface 701. Thus, the flesh surface 701 can be imaged by imaging the reflected light. The mist surface 702 can be imaged by imaging using white light (WL).

The normal light 3D image capture unit 341 of the imaging unit 302 (FIG. 3) performs stereoscopic image capturing using white light to acquire a 3D image of the mist surface 702. The special light 3D image capture unit 342 performs stereoscopic image capturing using infrared light to acquire a 3D image of the flesh surface 701. The difference between the two images is calculated to obtain thickness information of the mist 703 at each point.

Referring to FIG. 9, at a point P1, a depth to the mist surface 702 imaged using white light (WL) is denoted by depth WL_depth and a depth to the flesh surface 701 imaged using infrared light (IR) is denoted by depth IR_depth. In this case, thickness m_depth of the mist 703 at the point P1 can be represented by the following Equation 3.

$$\text{thickness } m\_depth = \text{depth IR\_depth} - \text{depth WL\_depth}$$

Figure 10:
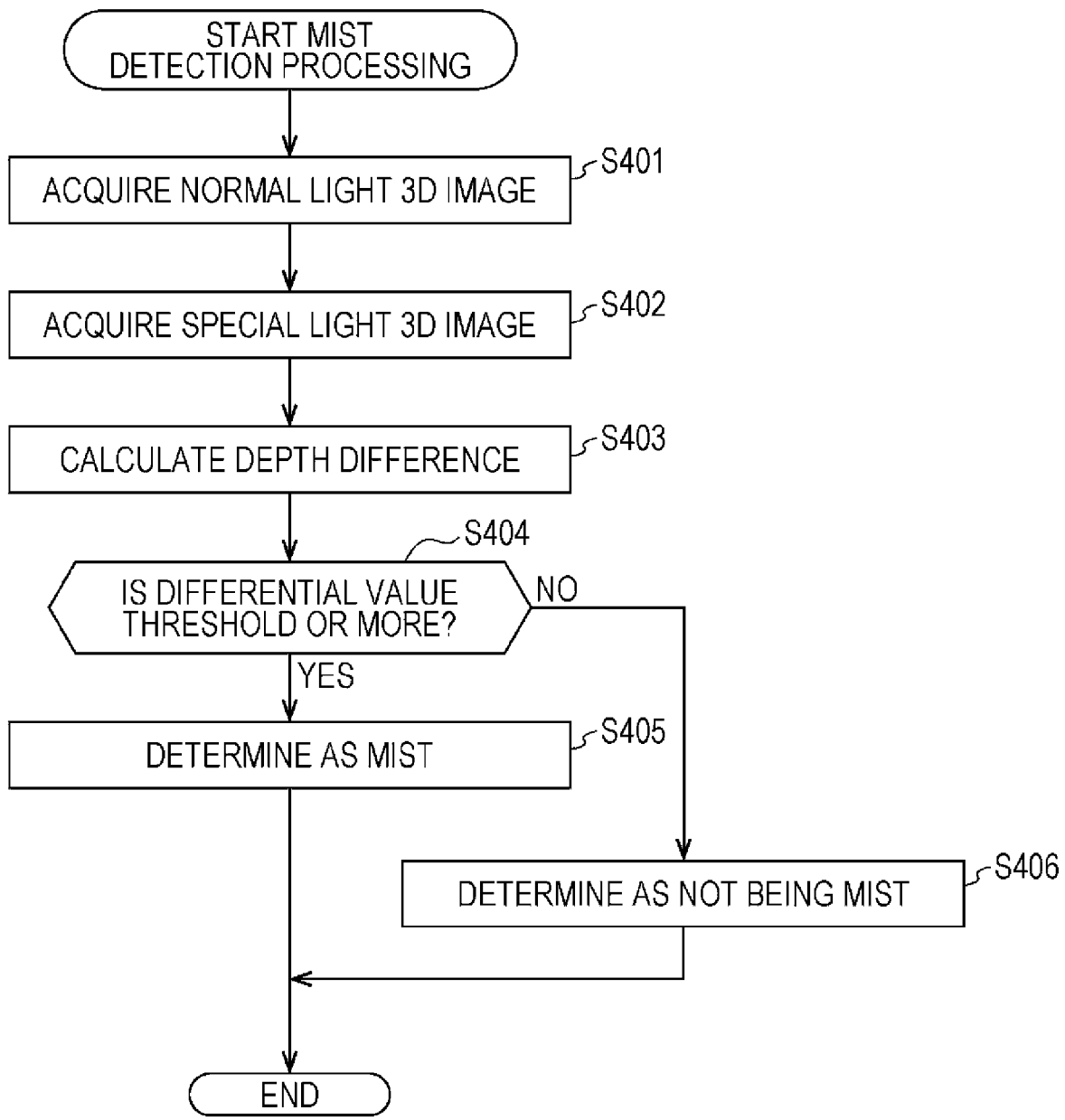
FIG. 10 is a flowchart for describing processing of the image processing apparatus when a mist is detected.

When the thickness m_depth obtained by such an arithmetic operation is greater than a predetermined threshold th, a mist is determined to be present. An operation of the image processing apparatus 301 (FIG. 3) which performs such processing is described with reference to a flowchart of FIG. 10.

In step S401, a normal light 3D image is acquired. In this case, the normal light 3D image capture unit 341 of the imaging unit 302 performs imaging with white light to acquire the normal light 3D image, and the acquired normal light 3D image is supplied to the 3D image acquisition unit 323.

In step S402, a special light 3D image is acquired. In this case, the special light 3D image capture unit 342 of the imaging unit 302 performs imaging with infrared light to acquire the special light 3D image, and the acquired special light 3D image is supplied to the 3D image acquisition unit 323.

In step S403, the depth information generation unit 124 calculates a depth difference. The depth difference is calculated by performing the arithmetic operation of the above Equation 3 using coordinates in the depth direction of the 3D images.

In step S404, it is determined whether the differential value calculated in step S403 is equal to or greater than the threshold. The determination may be made by the depth information generation unit 124 and the determined result may be supplied to the target region detection unit 125. Alternatively, the target region detection unit 125 may receive the supply of depth information (differential value) generated by the depth information generation unit 124 to make the determination.

When the differential value is determined to be equal to or greater than the threshold in step S404, the processing proceeds to step S405. In step S405, a current processing point at this point of time is set as a mist. The threshold is a value obtained by adding a predetermined value to a value taking unevenness of the flesh surface 701 into consideration.

On the other hand, when the differential value is determined to be less than the threshold in step S404, the processing proceeds to step S406. In step S406, a current processing point at this point of time is set as not being a mist.

When a mist is detected, alarm display for notifying a user of the presence of the mist or display in which a color representing the mist is superimposed on a part in which the mist has been detected is performed. Such display may be superimposed on a normal light image or a special light image. Further, the image to be superimposed may be a 3D image.

When the ratio of a region in which the mist has been detected to the entire image is large, an image of the flesh surface 701 with no mist may be provided to a user by black-and-white display using an IR light source (infrared light). Alternatively, image processing for removing the mist may be applied to an image to provide the image from which the mist has been removed to a user. This makes it possible to ensure an operative field to prevent an operation error.

In this manner, it is possible to obtain a differential value from two 3D images and detect a mist or a shine from the obtained differential value. Information about the detected mist is presented to a user. Thus, a user can recognize the presence of a mist, which is difficult to recognize merely by looking at the captured image, by browsing the information.

<Application to Detection of Artery and Vein>

Next, the processing of the image processing apparatus 301 is further described with a concrete example in which an artery or a vein is detected as a region to be detected. First, an image obtained by imaging an artery and a vein with a 2D normal light is described with reference to FIGS. 11A to 11C. Although, here, an artery and a vein are described as an example, the present embodiment is not limited to a combination of an artery and a vein. The present embodiment is applicable to blood vessels.

Figure 11:
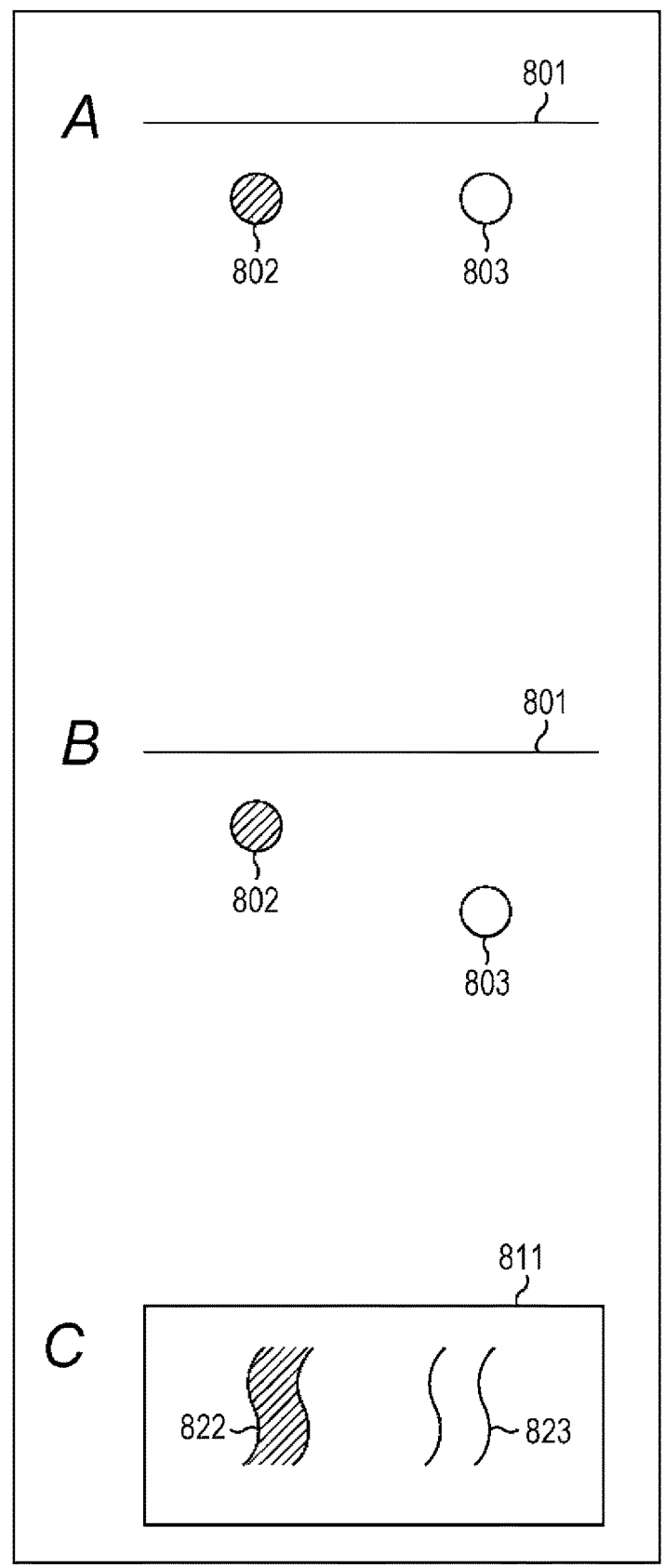
FIGS. 11A to 11C are diagrams for describing the positional relationship between an artery and a vein in a 2D image.

FIG. 11A illustrates a state in which a vein 802 and an artery 803 are located at the same depth in the depth direction under a surface 801. In FIGS. 11A to 11C, the vein is illustrated as a shaded circle and the artery is illustrated as a white circle. FIG. 11B illustrates a state in which the vein 802 and the artery 803 are located at different depths in the depth direction under the surface 801.

When the state illustrated in FIG. 11A and the state illustrated in FIG. 11B are imaged as a 2D image with normal light from the surface 801, an image 811 as illustrated in FIG. 11C is captured. In the image 811, a vein 812 and an artery 813 are imaged. Since the image 811 is a 2D image and information indicating the positional relationship between the vein 812 and the artery 813 is not displayed on the image 811, it is difficult to read which one is located at a deeper position between the vein 812 and the artery 813.

Figure 12:
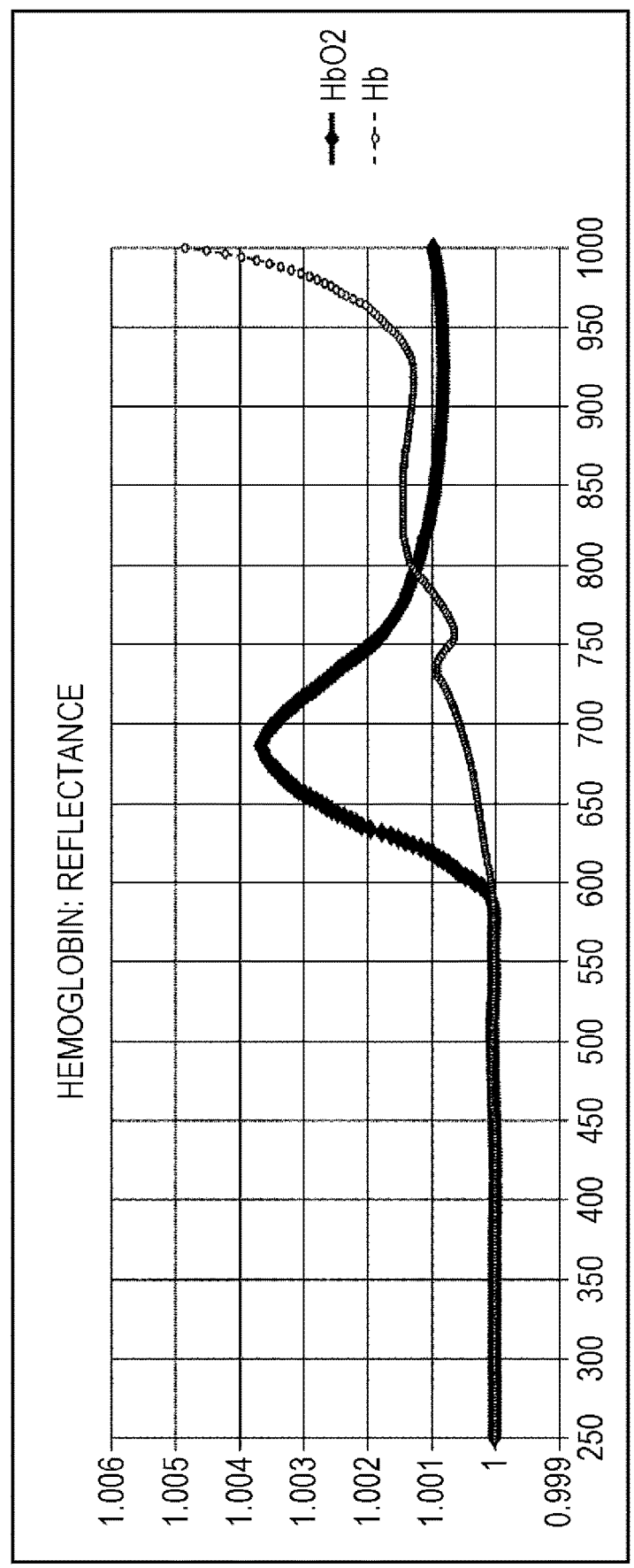
FIG. 12 is a diagram for describing the reflectance of hemoglobin.

FIG. 12 is a graph illustrating the reflectance in hemoglobin combined with oxygen ($HbO_2$) and the reflectance in hemoglobin separated from oxygen (Hb). In the graph of FIG. 12, the horizontal axis represents the wavelength of light to be applied and the vertical axis represents the reflectance.

The graph of FIG. 12 shows that hemoglobin combined with oxygen ($HbO_2$) and hemoglobin separated from oxygen (Hb) have different reflectance characteristics by the wavelength. Hemoglobin combined with oxygen ($HbO_2$) flows through an artery and hemoglobin separated from oxygen (Hb) flows through a vein.

When an artery and a vein are located at the same depth and have substantially the same thickness, the artery has a higher reflectance than the vein near a wavelength of 640 nm or larger to be more vivid red due to a difference in reflectance, and is thus distinguishable from the vein. However, when the vein is located near the surface and the vein is located at a slightly deep position, and the two blood vessels have substantially the same thickness as illustrated in FIG. 11B, light reflected by flesh tissues before reaching the vein increases to cause the vein to have the same degree of brightness as the artery when observed from the surface with normal light. Thus, it is difficult to distinguish between two blood vessels, specifically, a vein and an artery located at different depths.

Distinction between the vein 812 and the artery 813 may be made from the positional relationship in the depth direction therebetween. Thus, the positional relationship in the depth direction between blood vessels is important information. Therefore, as illustrated in FIG. 13, blood vessels located at different depths are imaged with different wavelengths.

First, 3D images are captured with two beams of light having different wavelengths. Here, the imaging is performed with a first wavelength $\lambda 1$ and a second wavelength $\lambda 2$. The beams of light having different wavelengths reach different depths within a flesh tissue. The first wavelength $\lambda 1$ reaches a relatively shallow part. The second wavelength $\lambda 2$ reaches a relatively deep part.

Figure 13:
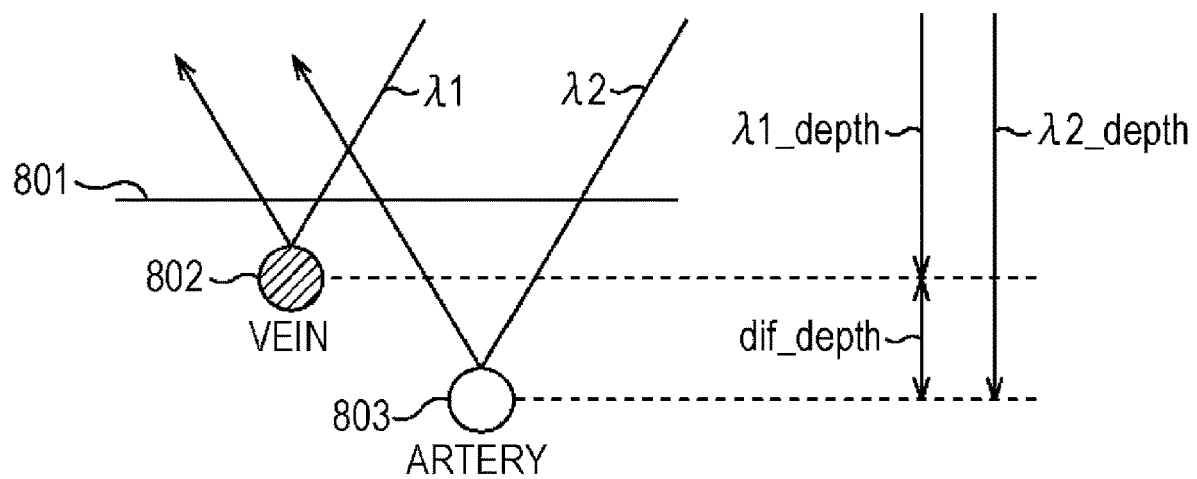
FIG. 13 is a diagram for describing a principle of detecting an artery and a vein.

As illustrated in FIG. 13, when imaging is performed with the vein 802 located near the surface 801 and the artery 803 located at a deep position, the first wavelength $\lambda 1$ is reflected by the vein 802, and the second wavelength $\lambda 2$ is reflected by the artery 803. That is, depth $\lambda 1\_depth$ as depth information of the vein 802 is acquired by stereoscopic image capturing with the first wavelength $\lambda 1$, and depth $\lambda 2\_depth$ as depth information of the artery 803 is acquired by stereoscopic image capturing with the second wavelength $\lambda 2$.

The distance between the two blood vessels can be obtained by calculating the difference between the two depths.

$$\text{distance dif\_depth} = \text{depth } \lambda 2\_depth - \text{depth } \lambda 1\_depth$$

The distance information between the blood vessels obtained in this manner is used to correct and display the reflectance of the artery located at a deep position. Accordingly, an image that enables distinction between the artery and the vein can be obtained.

Figure 14:
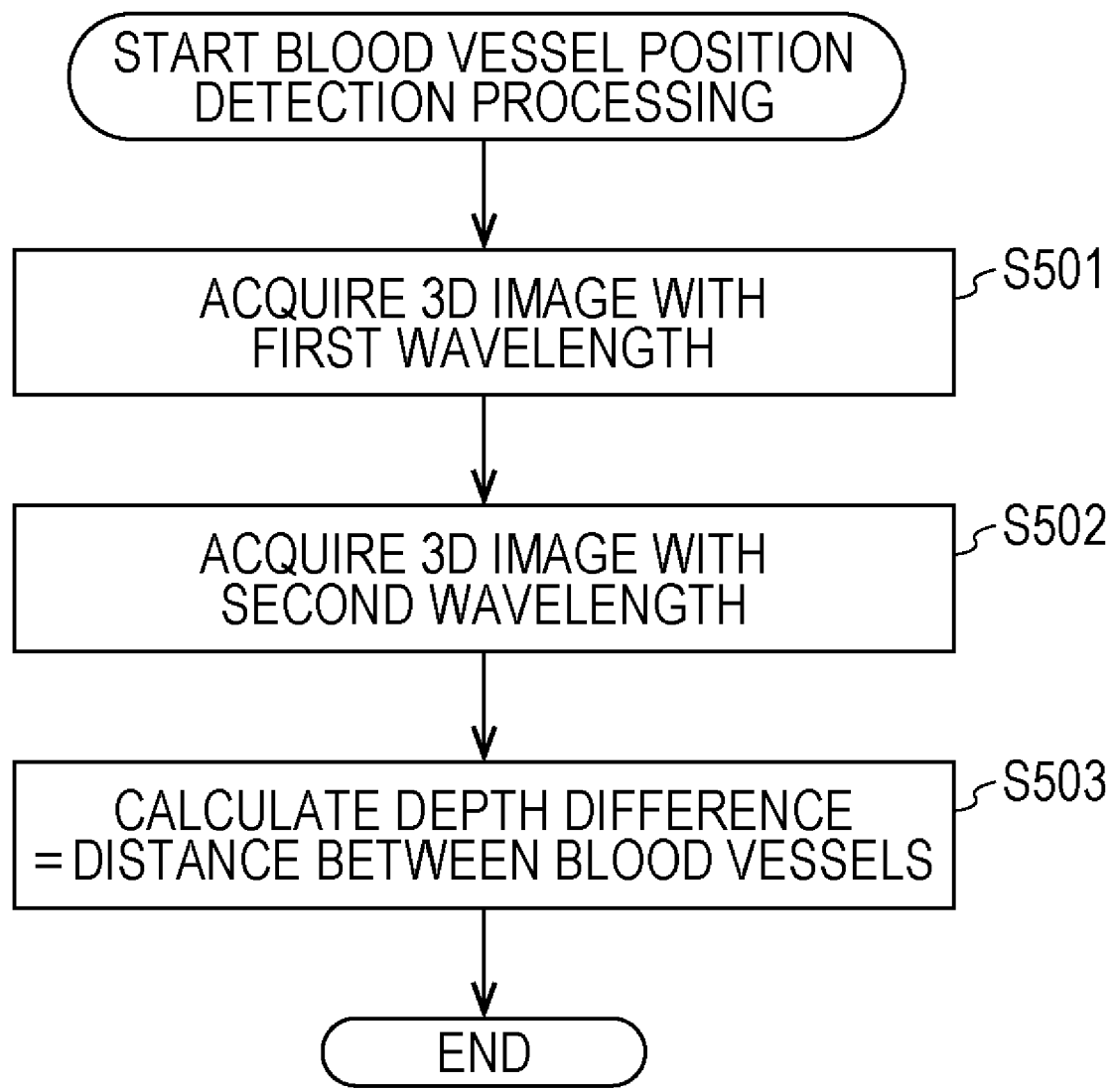
FIG. 14 is a flowchart for describing processing of the image processing apparatus when an artery and a vein are detected.

An operation of the image processing apparatus 301 (FIG. 3) which performs such processing is described with reference to a flowchart of FIG. 14.

In step S501, a 3D image captured with the first wavelength $\lambda 1$ is acquired. In this case, the special light 3D image capture unit 342 of the imaging unit 302 performs imaging with the first wavelength $\lambda 1$ to acquire the special light 3D image, and the acquired special light 3D image is supplied to the 3D image acquisition unit 323.

In step S502, a 3D image captured with the second wavelength $\lambda 2$ is acquired. In this case, the special light 3D image capture unit 342 of the imaging unit 302 performs imaging with the second wavelength $\lambda 2$ to acquire the special light 3D image, and the acquired special light 3D image is supplied to the 3D image acquisition unit 323.

In step S503, the depth information generation unit 124 calculates a depth difference.

The depth difference is calculated by performing the arithmetic operation of the above Equation 4 using coordinates in the depth direction of the 3D images. The calculated differential value is defined as the distance between the blood vessels.

An image that enables distinction between the artery and the vein can be obtained by correcting and displaying the reflectance of the artery located at a deep position using the distance between the blood vessels calculated in this manner. For example, a blood vessel located at a shallow position is displayed in red, and a blood vessel that can be determined to be located at a deeper position than the shallow blood vessel from distance information is displayed in slightly dark red to perform coloring corresponding to the depth. Accordingly, an image that enables a user to recognize the positional relationship between blood vessels corresponding to the depth at a glance is presented.

Such an image may be superimposed on a normal light image or a special light image to be presented to a user. Alternatively, the image may be superimposed on a 3D image.

In this manner, it is possible to obtain a differential value from two 3D images and detect the positional relationship (depth information) between blood vessels from the obtained differential value. The detected positional information is presented to a user. Thus, a user can recognize the positional relationship between the blood vessels, which is difficult to recognize merely by looking at the captured image, by browsing the information.

<Application to Detection of Overlapping State of Blood Vessels>

Next, the processing of the image processing apparatus 301 is further described with a concrete example in which an overlapping state of blood vessels is detected as a region to be detected. First, an overlapping state of blood vessels is described with reference to FIG. 15.

For example, the deep part of a mucous membrane or placental blood vessels in turbid amniotic fluid can be observed by excitation light observation after indocyanine green (ICG) injection. However, in a part having a plurality of overlapping blood vessels as illustrated in the left figure in FIG. 15, it is difficult to determine an overlapping state of the blood vessels. Thus, the exit of a blood vessel that is connected to a cancer tissue 911 and thus has metastatic potential may be erroneously determined to be the exit of another blood vessel.

Figure 15:
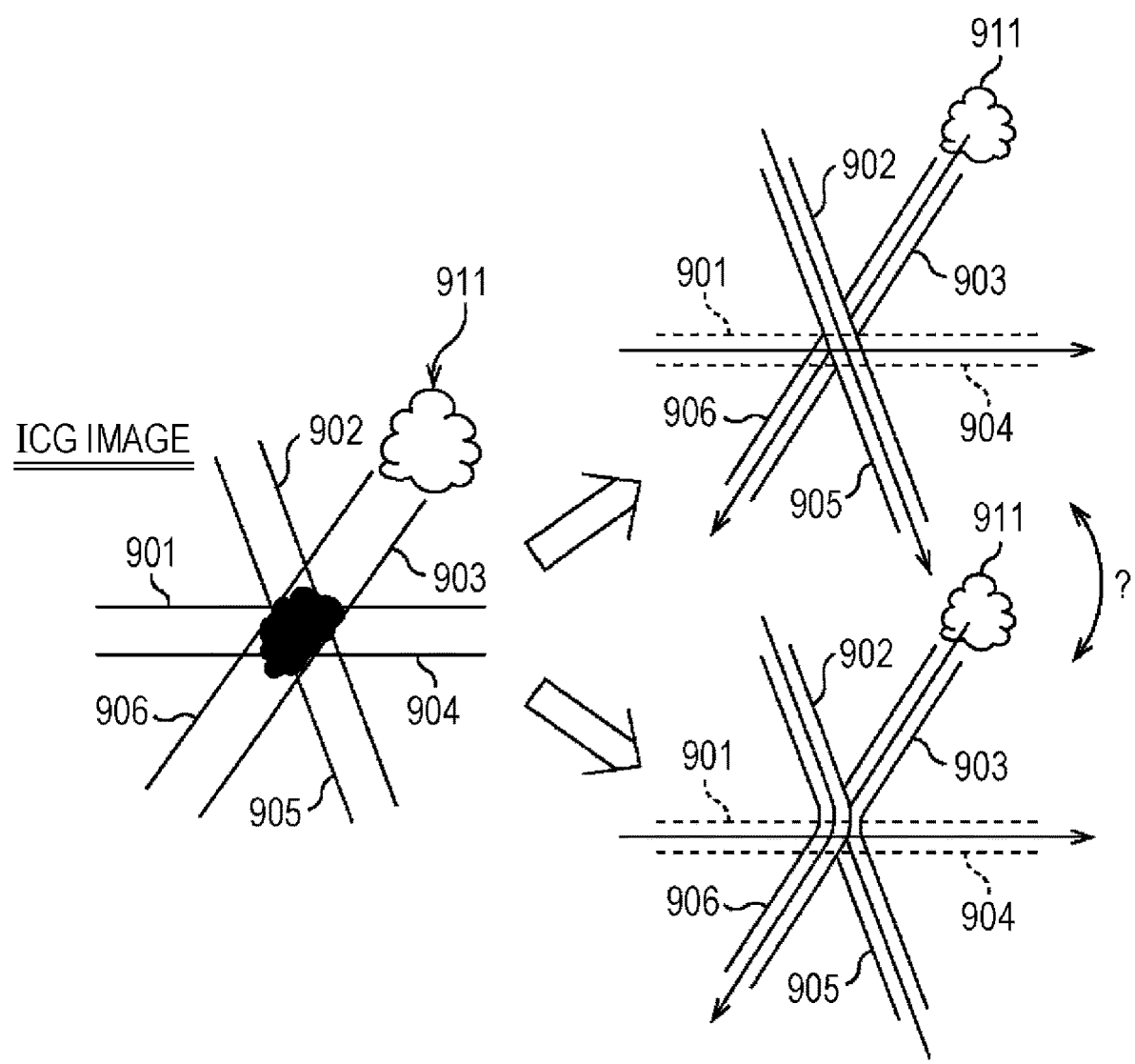
FIG. 15 is a diagram for describing determination of overlapping of blood vessels.

In the left figure in FIG. 15, a blood vessel 901, a blood vessel 902, and a blood vessel 903 overlap each other on the central part in the figure. Thus, it is difficult to determine whether the blood vessels are connected as illustrated in the upper right figure in FIG. 15 or the blood vessels are connected as illustrated in the lower right figure in FIG. 15.

The upper right figure in FIG. 15 illustrates a state when it is determined that the blood vessel 901 and a blood vessel 904 are connected, the blood vessel 902 and a blood vessel 905 are connected, and the blood vessel 903 and a blood vessel 906 are connected. Based on such determination, the blood vessel 903 and the blood vessel 906 are connected to the cancer tissue 911.

The lower right figure in FIG. 15 illustrates a state when it is determined that the blood vessel 901 and the blood vessel 904 are connected, the blood vessel 902 and the blood vessel 906 are connected, and the blood vessel 903 and the blood vessel 905 are connected. Based on such determination, the blood vessel 903 and the blood vessel 905 are connected to the cancer tissue 911.

In this manner, when an overlapping state is not correctly determined, connection of blood vessels may be erroneously determined. Thus, it is important to present an overlapping state between blood vessels to a user to enable the user to determine connection of the blood vessels.

Thus, stereoscopic image capturing is performed under irradiation with excitation light after ICG injection to detect distance information ICG_depth. Then, connection and overlapping of blood vessels (that is, distinction between different blood vessels) are detected from the detected distance information ICG_depth. Further, the direction of a blood flow is determined from the blood vessel overlapping information to estimate a region having a high metastatic potential of a cancer tissue.

Figure 16:
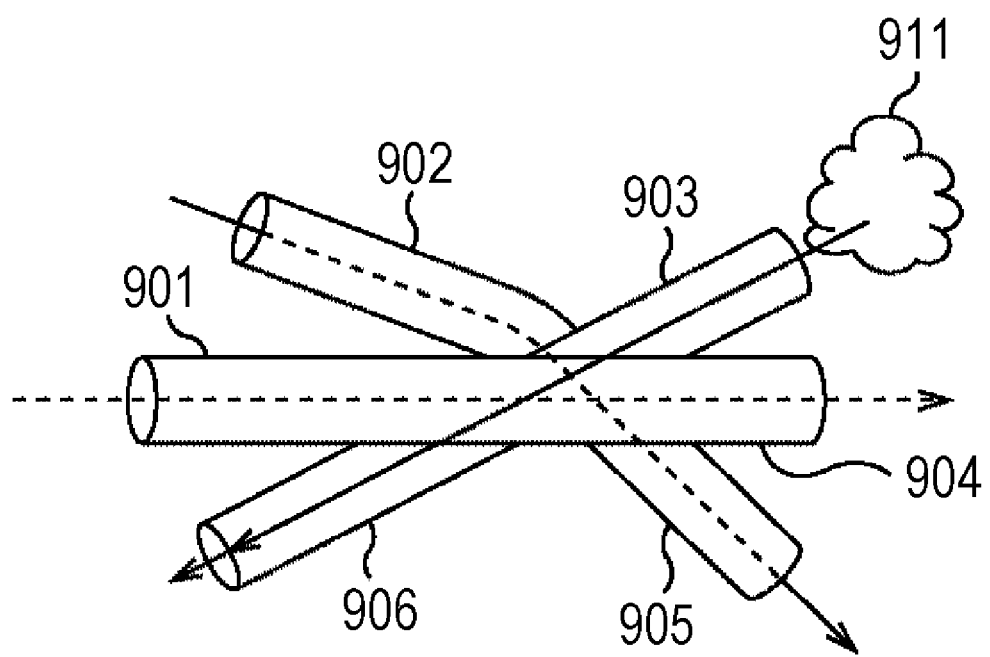
FIG. 16 is an image example taking the positional relationship between blood vessels into consideration.

For example, an image as illustrated in FIG. 16 is presented to a user. The image example illustrated in FIG. 16 displays that the blood vessel 901 and the blood vessel 904 are connected, the blood vessel 902 and the blood vessel 905 are connected, and the blood vessel 903 and the blood vessel 906 are connected. The connection of the blood vessels are detected in such a manner that stereoscopic image capturing is performed under irradiation with excitation light after ICG injection to detect distance information ICG_depth, and the connection and overlapping of the blood vessels are detected from the detected distance information ICG_depth.

Further, the positional relationship between the blood vessels, specifically, the blood vessel 901 and the blood vessel 904 are located on the top, the blood vessel 902 and the blood vessel 905 are located on the bottom, and the blood vessel 903 and the blood vessel 906 are interposed therebetween, is also detected from the distance information ICG_depth. Thus, display that makes such a positional relationship clear is performed.

For example, in the display of overlapping blood vessels, different blood vessels are displayed with different brightnesses or colors to enable a user to easily determine the blood vessel structure. A region that has metastatic potential of cancer may be estimated from connection information of a blood vessel connected to the cancer tissue 911, and the region may be highlighted.

Such display (presentation of an image) enables a user to correctly determine an overlapping state of blood vessels. Thus, an infiltrated blood vessel/tissue can be correctly removed. Further, it is possible to reduce overlook of a region that has metastatic potential of cancer.

Figure 17:
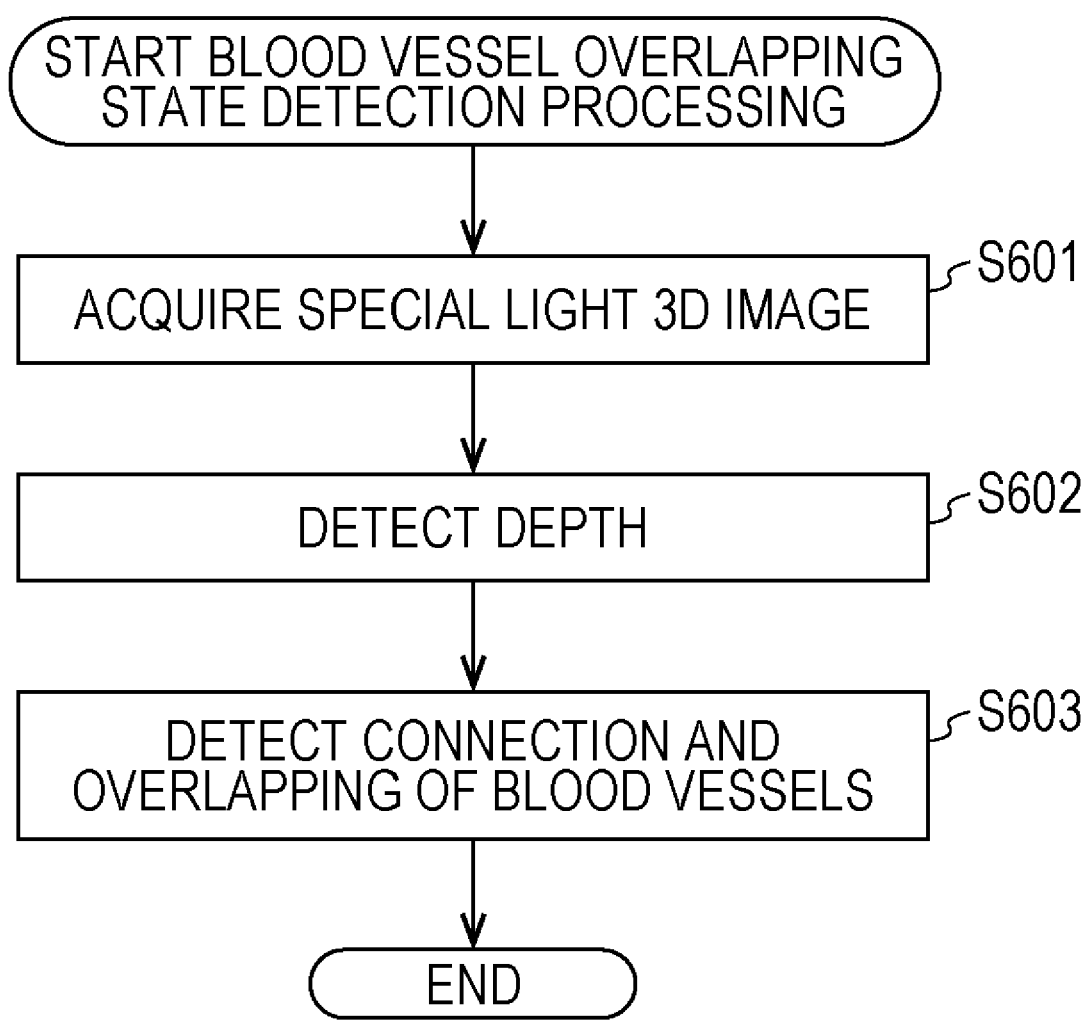
FIG. 17 is a flowchart for describing processing of the image processing apparatus when overlapping of blood vessels is detected.

An operation of the image processing apparatus 301 (FIG. 3) which performs such processing is described with reference to a flowchart of FIG. 17.

In step S601, a 3D image is acquired by excitation light image capturing. In this case, the special light 3D image capture unit 342 of the imaging unit 302 performs imaging with excitation light after ICG injection to acquire the special light 3D image, and the acquired special light 3D image is supplied to the 3D image acquisition unit 323.

In step S602, the depth information generation unit 124 calculates a depth difference.

In step S603, connection and overlapping of blood vessels are detected. The connection and the overlapping of blood vessels are detected in such a manner that the 3D image acquired by the excitation light image capturing is analyzed to detect a vertical positional relationship between the blood vessels from the depth information of each blood vessel in a part in which the blood vessels overlap each other or to estimate the connection of blood vessels located at substantially the same depth from the depth information.

As described above, different blood vessels can be displayed with different brightnesses or colors or a region that has metastatic potential of cancer can be highlighted using the detected result. Thus, a user can correctly determine an overlapping state of blood vessels. As a result, an infiltrated blood vessel/tissue can be correctly removed. Further, it is possible to reduce overlook of a region that has metastatic potential of cancer.

<Application to Detection of Tumor>

Next, the processing of the image processing apparatus 301 is further described with a concrete example in which a tumor is detected as a region to be detected. First, estimation of the volume of a tumor is described with reference to FIG. 18.

In photodynamic diagnosis (PDD), observation is performed with blue light after a patient takes aminolevulinic acid (5-ALA), and a tumor looks like emitting red light. In this PDD, only a planar image can be observed. Thus, it is difficult for a user to recognize a real size of a tumor.

Figure 18:
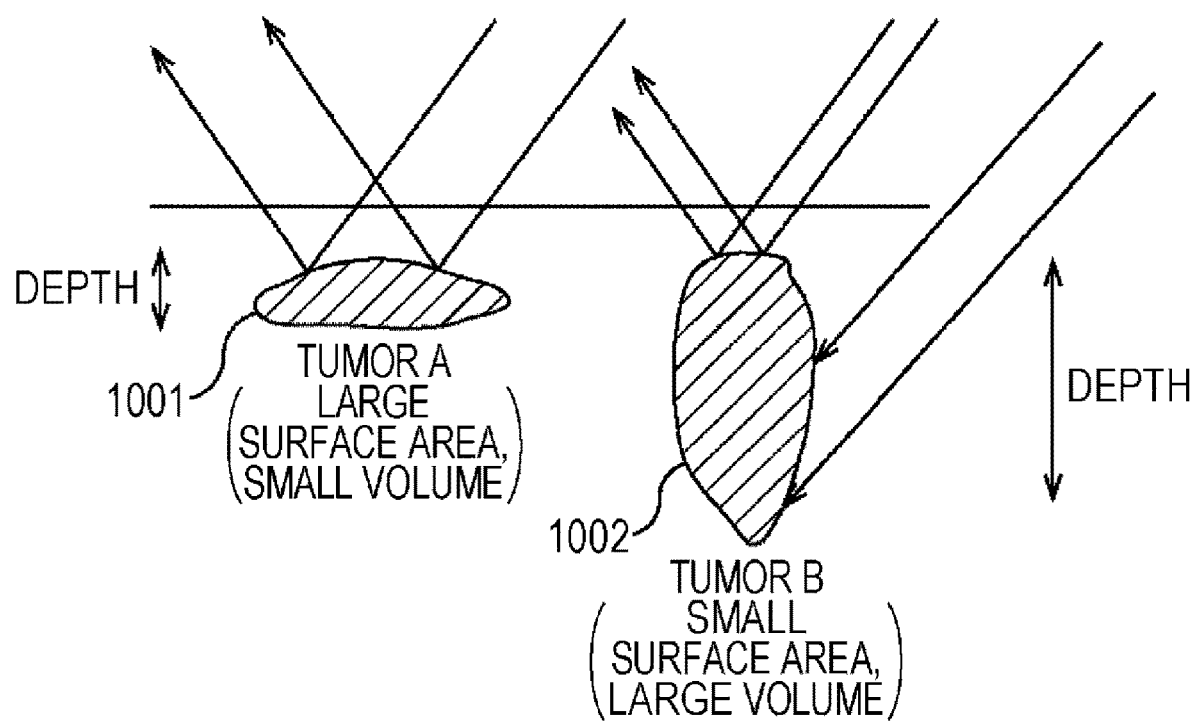
FIG. 18 is a diagram for describing a principle of detecting the volume of a tumor.

For example, as illustrated in FIG. 18, a tumor may be a tumor 1001 which has a planar expansion, but does not infiltrate deep in an inner face direction, or may be a tumor 1002 which has little planar expansion, but infiltrates deep in the inner face direction. It is difficult to determine whether a tumor infiltrates deep as with the tumor 1002 only with a planar image.

Thus, stereoscopic image capturing is performed under PDD to detect distance information PDD_depth, and the volume of a tumor is estimated from the surface area of the tumor obtained from a 2D image and the distance information PDD_depth. A result of the volume estimation performed in this manner is presented to a user by, for example, highlighting a tumor having a large estimated volume.

A tumor that has a small surface area on a 2D image and has a large estimated volume may be highlighted in a further distinguishable manner. Such display enables a user to correctly distinguish a tumor having a large volume which is likely to be brought to follow-up due to its small surface area and to determine an appropriate treatment.

Figure 19:
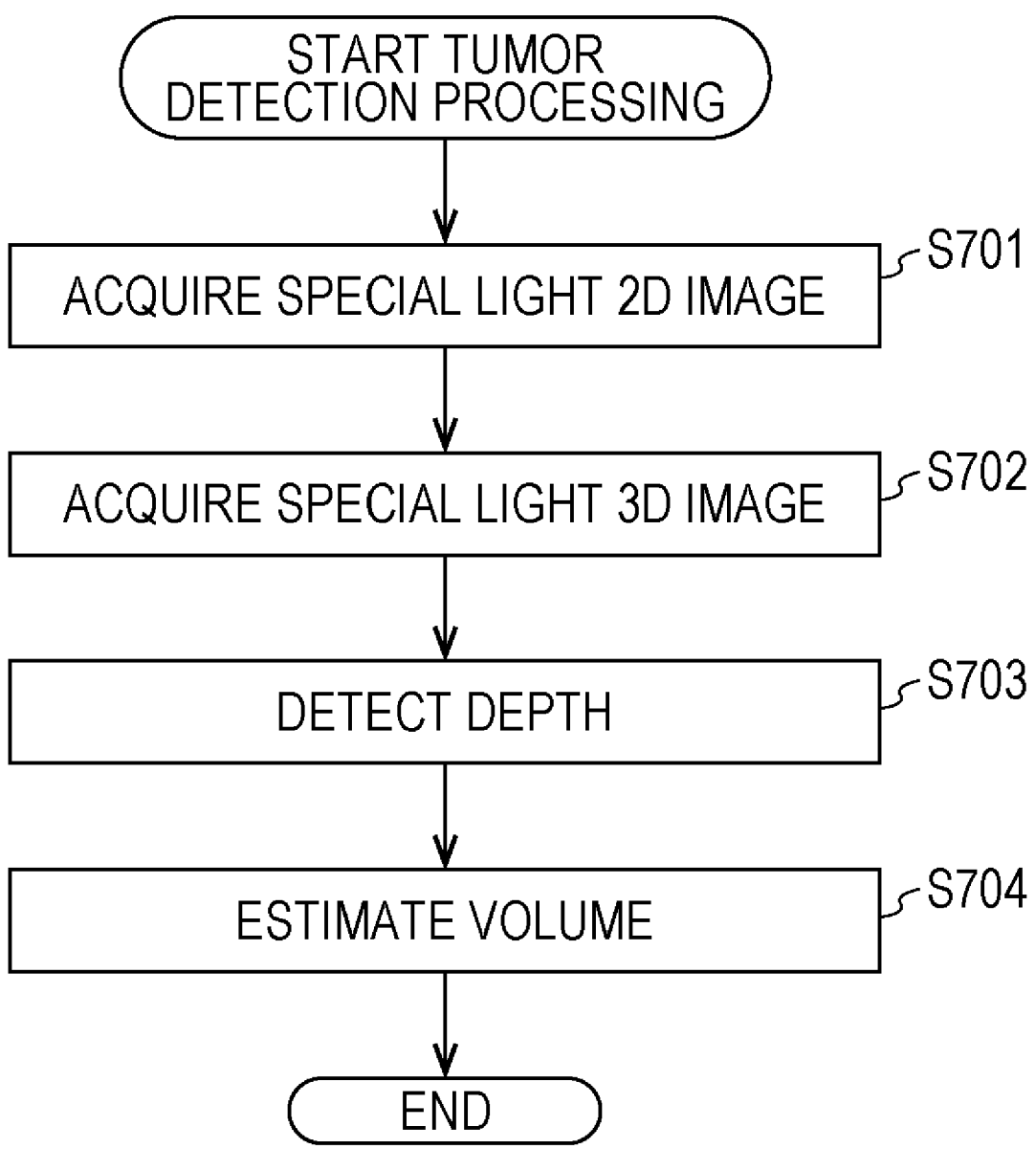
FIG. 19 is a flowchart for describing processing of the image processing apparatus when the volume of a tumor is detected.

An operation of the image processing apparatus 301 (FIG. 3) which performs such processing is described with reference to a flowchart of FIG. 19.

In step S701, a 2D image is acquired by imaging under PDD. In this case, the special light 3D image capture unit 342 of the imaging unit 302 performs stereoscopic imaging under irradiation with blue light after a patient takes aminolevulinic acid to acquire a special light 3D image in which an affected part is colored in red. The acquired 3D image is converted into the 2D image to acquire the 2D image.

In step S702, a 3D image is acquired by imaging under PDD. As with step S701, the special light 3D image capture unit 342 of the imaging unit 302 performs stereoscopic imaging under irradiation with blue light after a patient takes aminolevulinic acid to acquire the special light 3D image in which an affected part is colored in red.

In step S703, the depth information generation unit 124 calculates the depth of a tumor (the depth in the inner face direction) using the acquired special light 3D image.

In step S704, the volume of the tumor is estimated. The surface area is calculated from the acquired special light 2D image and multiplied by the depth information calculated from the 3D image to estimate the volume of the tumor.

In accordance with the volume estimated in this manner, as described above, a tumor having a large estimated volume is, for example, highlighted to be presented to a user. Such display enables a user to correctly determine the size of the tumor and determine an appropriate treatment.

In this manner, the present technology makes it possible to detect a target region and a feature amount related thereto, which are difficult to detect by detection processing only with a 2D image. Further, a user can obtain more pieces of information in an easily visually recognizable form by performing highlighting processing or image superimposing processing based on the detected target region and feature amount on the presented image.

This makes it possible to achieve more accurate diagnosis before, during and after an operation, improvement in the accuracy of an operation, reduction in operation time, and minimally invasive operation.

The above detection operations of the specific regions may be performed independently or in combination. For example, since the detection of an artery and a vein and the detection of an overlapping state of blood vessels are both blood vessel detection operations, these detection operations may be performed in combination to more appropriately detect an artery and a vein and clearly detect the positional relationship between the artery and the vein.

Further, the detection operations of different regions may be switched to be performed. For example, a transparent membrane and a mist may be sequentially detected and the presence of the transparent membrane and the mist may be presented to a user, and detection of a tumor may also be performed.

<Recording Medium>

The above series of processing may be executed by hardware or software. When the series of processing is executed by software, a program constituting the software is installed in a computer. The computer includes a computer incorporated into dedicated hardware and, for example, a general personal computer capable of executing various functions by installing various programs therein.

Figure 20:
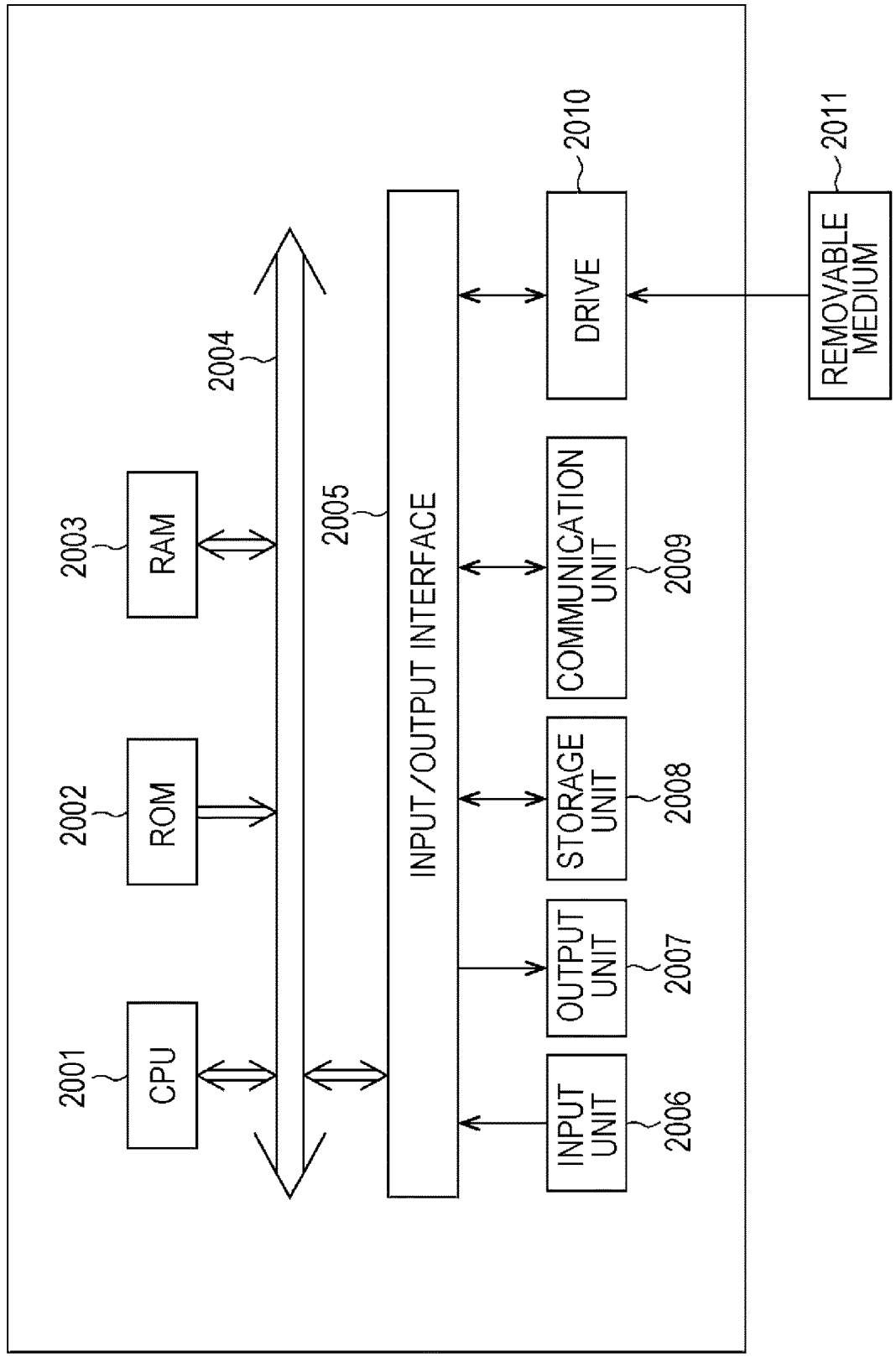
FIG. 20 is a diagram for describing a recording medium.

FIG. 20 is a block diagram illustrating an example of the configuration of hardware of a computer which executes the above series of processing by a program. In the computer, a central processing unit (CPU) 2001, a read only memory (ROM) 2002, and a random access memory (RAM) 2003 are connected to each other through a bus 2004. Further, an input/output interface 2005 is connected to the bus 2004. An input unit 2006, an output unit 2007, a storage unit 2008, a communication unit 2009, and a drive 2010 are connected to the input/output interface 2005.

The input unit 2006 includes a keyboard, a mouse, and a microphone. The output unit 2007 includes a display and a speaker. The storage unit 2008 includes a hard disk and a nonvolatile memory. The communication unit 2009 includes a network interface. The drive 2010 drives a removable medium 2011 which includes a magnetic disk, an optical disk, a magneto-optical disk, and a semiconductor memory.

In the computer having the above configuration, for example, the CPU 2001 loads a program stored in the storage unit 2008 to the RAM 2003 through the input/output interface 2005 and the bus 2004 to execute the program to perform the above series of processing.

For example, the program executed by the computer (CPU 2001) may be provided by recording the program in the removable medium 2011 as a package medium. Alternatively, the program may be provided through a wired or wireless transmission medium such as a local area network (LAN), Internet, and digital satellite broadcasting.

In the computer, the program may be installed in the storage unit 2008 through the input/output interface 2005 by attaching the removable medium 2011 to the drive 2010. Alternatively, the program may be received by the communication unit 2009 through a wired or wireless transmission medium and installed in the storage unit 2008. Alternatively, the program may be previously installed in the ROM 2002 or the storage unit 2008.

The program executed by the computer may be a program in which processing is performed in a time-series manner along the order described in the present specification, or processing is performed in parallel or at necessary timing, for example, when called.

In the present specification, the system represents the entire apparatus that includes a plurality of apparatuses.

The effects described in the present specification are merely examples, and the effects of the present technology are not limited thereto. The present technology may have another effect.

The embodiment of the present technology is not limited to the embodiment described above. Various modifications may be made without departing from the gist of the present technology.

The present technology may have the following configuration.

(1)

A medical system including a medical imaging device, and an image processing apparatus for processing an image captured by the medical imaging device. The image processing apparatus includes: circuitry configured to acquire a special light image from the image captured by the medical imaging device, the special light image having information limited to a specific wavelength band, generate depth information at a predetermined position of a patient using the special light image, and detect a structural relationship using the depth information.

(2)

The medical system according to (2), wherein the medical imaging device is an endoscope or a microscope.

(3)

The medical system according to (1) or (2), wherein the structural relationship includes a bleeding position, a transparent membrane thickness, a mist resulting from surgery, and/or an overlapping state of blood vessels.

(4)

The medical system according to (1) or (2), wherein the circuitry is further configured to acquire a normal light image having information limited to a white light wavelength band, the specific wavelength band corresponds to infrared light, and detect a bleeding position based on additional depth information generated using both the special light image and the normal light image.

(5)

The medical system according to (1) or (2), wherein the circuitry is further configured to generate an image in which a predetermined mark or text representing the bleeding point is superimposed on the special light image or the normal light image.

(6)

The medical system according to (1) or (2), wherein the circuitry is further configured to acquire a normal light image having information limited to a white light wavelength band, the specific wavelength band corresponding to polarized light, and detect a membrane thickness of a transparent membrane based on additional depth information generated using both the special light image and the normal light image.

(7)

The medical system according to (6), wherein the circuitry is further configured to generate an image in which a numerical value indicating the membrane thickness of the transparent membrane or a gradation image corresponding to the membrane thickness, is superimposed on the special light image or the normal light image.

(8)

The medical system according to (1) or (2), wherein the circuitry is further configured to acquire a normal light image having information limited to a white light wavelength band, the specific wavelength band corresponding to infrared light, and detect a mist resulting from surgery based on additional depth information generated using both the special light image and the normal light image.

(9)

The medical system according to (8), wherein the circuitry is further configured to generate an image in which alarm display that notifies the presence of the mist or a color that represents the mist, is superimposed on the special light image or the normal light image.

(10)

The medical system according to (9), wherein the circuitry is further configured to instruct display of the special light image or generates an image via image processing that removes the mist resulting from the surgery.

(11)

The medical system according to (1) or (2), wherein the specific wavelength band includes a first wavelength and a second wavelength different from the first wavelength, and the circuitry is further configured to detect positional information in a depth direction of a blood vessel based on additional depth information generated using a first special light image having information limited to the first wavelength and a second special light image having information limited to the second wavelength.

(12)

The medical system according to (12), wherein the circuitry is further configured to generate an image in which a reflectance of an artery located at a deeper position than a vein is corrected using the positional information in the depth direction of the blood vessel.

(13)

The medical system according to (1) or (2), wherein the specific wavelength band corresponds to excitation light used in excitation light observation after indocyanine green (ICG) injection, the circuitry is further configured to generate depth information at the predetermined position from a depth image obtained by the excitation light, and the circuitry is further configured to detect a positional relationship between overlapping blood vessels, a blood vessel connected to a cancer tissue, or a region having metastatic potential of cancer from the depth information.

(14)

The medical system according to (13), wherein the circuitry is further configured to generate an image in which overlapping blood vessels are displayed with different brightnesses or colors or an image, in which a region having metastatic potential of cancer, is highlighted.

(15)

The medical system according to (1) or (2), wherein the specific wavelength band corresponds to blue light, circuitry is further configured to generate depth information at the predetermined position from a depth image obtained by the blue light, and circuitry is further configured to estimate the size in a planar direction of a tumor from an image obtained by the blue light and detect the volume of the tumor by multiplying a value of the estimated size by the depth information.

(16)

The medical system according to (15), wherein the circuitry is further configured to generate an image in which the tumor having volume above a predetermined threshold is highlighted.

(17)

The medical system according to (1) or (2), wherein the circuitry is further configured to acquire a normal light image having information limited to a white light wavelength band, wherein circuitry is further configured to generate a special light image having information limited to the specific wavelength band from the normal light image.

(18)

The medical system according to (1) or (2), further including a special light source configured to generate the special light for illuminating the predetermined position of the patient.

(19)

The medical system according to (1) or (2), wherein the depth information is generated with respect to a direction into a body of the patient or with respect to a direction away from the body of the patient depending on the structural relationship.

(20)

An image processing method including acquiring a special light image, from the image captured by the medical imaging device, the special light image having information limited to a specific wavelength band; generating depth information at a predetermined position of a patient using the special light image; and detecting a structural relationship using the depth information.

(21)

A non-transitory computer readable medium having stored thereon a program that when executed by a computer causes the computer to execute processing, the processing including acquiring a special light image, from the image captured by the medical imaging device, the special light image having information limited to a specific wavelength band; generating depth information at a predetermined position of a patient using the special light image; and detecting a structural relationship using the depth information.

(22)

An image processing apparatus for processing an image captured by the medical imaging device, the apparatus including circuitry configured to acquire a special light image from the image captured by the medical imaging device, the special light image having information limited to a specific wavelength band, generate depth information at a predetermined position of a patient using the special light image, and detect a structural relationship using the depth information.

REFERENCE SIGNS LIST

101 Image processing apparatus
102 Imaging unit
103 Display unit
121 Normal light image acquisition unit
122 Special light image acquisition unit
123 3D image acquisition unit
124 Depth information generation unit
125 Target region detection unit
126 Image generation unit
141 Normal light image capture unit
142 Special light image capture unit
143 3D image capture unit
222 Special light image acquisition unit
321 Normal light image acquisition unit
322 Special light image acquisition unit
323 3D image acquisition unit
341 Normal light 3D image capture unit
342 Special light 3D image capture unit

The invention claimed is:

1. A medical system comprising:
a medical imaging device;
a light source that outputs an observation band light or a specific band light having a narrower wavelength band than the observation band light; and
an image processing apparatus for processing an image captured by the medical imaging device, comprising:
circuitry configured to
acquire a first three-dimensional information generated based on a specific band light image captured by the medical imaging device when the light source outputs the specific band light and a second three-dimensional information generated based on an observation band light image captured by the medical imaging device when the light source outputs the observation band light, the specific band light image and the observation band light image being taken at a predetermined position and at different depths in a body of a patient, and
detect a thickness, a volume, or an overlap of components at the predetermined position of the patient in a depth direction based on a difference in the depth direction between the first three-dimensional information and the second three-dimensional information,
on condition that the thickness exceeds a thickness threshold, the circuitry is configured to highlight the predetermined position on the specific band light image and/or on the observation band light image,
on condition that the volume at the predetermined position exceeds a volume threshold, the circuitry is configured to highlight the predetermined position on the specific band light image and/or on the observation band light image, or
on condition that the components overlap, the circuitry is configured to superimpose a color or brightness on one of the components at the predetermined position on the specific band light image and/or on the observation band light image.

2. The medical system according to claim 1, wherein the medical imaging device is an endoscope or a microscope.

3. The medical system according to claim 1, wherein the thickness, the volume, and/or the overlap indicate bleeding position, a transparent membrane thickness, a mist resulting from surgery, and/or an overlapping state of blood vessels.

4. The medical system according to claim 1, wherein
the wavelength band of the specific band light corresponds to infrared light,
and
the circuitry is further configured to, on condition that the thickness exceeds the thickness threshold, detect a bleeding position.

5. The medical system according to claim 4, wherein the circuitry is further configured to, on condition that the thickness exceeds the thickness threshold, highlight the predetermined position using a predetermined mark or text representing the bleeding position.

6. The medical system according to claim 1, wherein the circuitry is further configured to
detect a membrane thickness of a transparent membrane.

7. The medical system according to claim 6, wherein the circuitry is further configured to highlight the predetermined position using a numerical value indicating the membrane thickness of the transparent membrane or to superimpose a gradation image corresponding to the membrane thickness.

8. The medical system according to claim 1, wherein the circuitry is further configured to
detect a mist resulting from surgery.

9. The medical system according to claim 8, wherein the circuitry is further configured to highlight the predetermined position using an alarm display that indicates presence of the mist or a color that represents the mist.

10. The medical system according to claim 9, wherein the circuitry is further configured to instruct display of the specific band light image or generates an image via image processing that removes the mist resulting from the surgery.

11. The medical system according to claim 1, wherein
the wavelength band of the specific band light includes a first wavelength and a second wavelength different from the first wavelength, and
the circuitry is further configured to detect positional information in the depth direction of a blood vessel based on additional depth information generated using a first specific band light image having information limited to the first wavelength and a second specific band light image having information limited to the second wavelength.

12. The medical system according to claim 11, wherein the circuitry is further configured to correct an image in which a reflectance of an artery located at a deeper position than a vein using the positional information in the depth direction of the blood vessel.

13. The medical system according to claim 1, wherein
the wavelength band of the specific band light corresponds to excitation light,
the circuitry is further configured to generate depth information from a depth image obtained by the excitation light, and
the circuitry is further configured to detect a positional relationship between overlapping blood vessels, a blood vessel connected to a cancer tissue, or a region having metastatic potential of cancer from the depth information.

14. The medical system according to claim 13, wherein the components are blood vessels, a thickness exceeding the thickness threshold indicates a region having metastatic potential of cancer, or a volume exceeding the volume threshold indicates a region having metastatic potential of cancer.

15. The medical system according to claim 1, wherein
the wavelength band of the specific band light corresponds to blue light,
the circuitry is further configured to generate depth information from a depth image obtained by the blue light, and
the circuitry is further configured to estimate a size in a planar direction of a tumor from an image obtained by the blue light and detect the volume of the tumor by multiplying a value of the estimated size by the depth information.

16. The medical system according to claim 15, wherein the circuitry is further configured to, on condition that the volume exceeds the volume threshold, generate an image in which the tumor is highlighted.

17. The medical system according to claim 1, wherein the observation band light a white light wavelength band, and wherein the circuitry is further configured to generate the specific band light image from the observation band light image.

18. The medical system according to claim 1, wherein the depth direction is with respect to a direction into the body of the patient or with respect to a direction away from the body of the patient.

19. An image processing method comprising:
irradiating an observation band light or a specific band light having a narrower wavelength band than the observation band light;
acquiring a first three-dimensional information generated based on a specific band light image captured when the specific band light is irradiated and a second three-dimensional information generated based on an observation band light image captured when the observation band light is irradiated, the specific band light image and the observation band light image being taken at a predetermined position and at different depths in a body of a patient;
detecting a thickness, a volume, or an overlap of components at the predetermined position of the patient in a depth direction based on a difference in the depth direction between the first three-dimensional information and the second three-dimensional information;
on condition that the thickness exceeds a thickness threshold, highlighting the predetermined position on the specific band light image and/or on the observation band light image;
on condition that the volume at the predetermined position exceeds a volume threshold, highlighting the predetermined position on the specific band light image and/or on the observation band light image, or
on condition that the components overlap, superimposing a color or brightness on one of the overlapping components at the predetermined position on the specific band light image and/or on the observation band light image.

20. A non-transitory computer readable medium having stored thereon a program that when executed by a computer causes the computer to execute processing, the processing comprising:
irradiating an observation band light or a specific band light having a narrower wavelength band than the observation band light;
acquiring a first three-dimensional information generated based on a specific band light image captured when the specific band light is irradiated and a second three-dimensional information generated based on an observation band light image captured when the observation band light is irradiated, the specific band light image and the observation band light image being taken at a predetermined position and at different depths in a body of a patient;
detecting a thickness, a volume, or an overlap of components at the predetermined position of the patient in a depth direction based on a difference in the depth direction between the first three-dimensional information and the second three-dimensional information;
on condition that the thickness exceeds a thickness threshold, highlighting the predetermined position on the specific band light image and/or on the observation band light image;
on condition that the volume at the predetermined position exceeds a volume threshold, highlighting the predetermined position on the specific band light image and/or on the observation band light image, or on condition that the components overlap, superimposing a color or brightness on one of the overlapping components at the predetermined position on the specific band light image and/or on the observation band light image.

21. An image processing apparatus for processing an image captured by medical imaging device, comprising:
a light source that outputs an observation band light or a specific band light having a narrower wavelength band than the observation band light; and
circuitry configured to
acquire a first three-dimensional information generated based on a specific band light image when the light source outputs the specific band light and a second three-dimensional information generated based on an observation band light image when the light source outputs the observation band light, the specific band light image and the observation band light image being taken at a predetermined position and at different depths in a body of a patient,
detect a thickness, a volume, or an overlap of components at the predetermined position of a patient in a depth direction based on the first three-dimensional information and the second three-dimensional information,
on condition that the thickness exceeds a thickness threshold, the circuitry is configured to highlight the predetermined position on the specific band light image and/or on the observation band light image,
on condition that the volume at the predetermined position exceeds a volume threshold, the circuitry is configured to highlight the predetermined position on the specific band light image and/or on the observation band light image, or
on condition that the components overlap, the circuitry is configured to superimpose a color or brightness on one of the components at the predetermined position on the specific band light image and/or on the observation band light image.

22. The image processing apparatus according to claim 21, wherein the components are blood vessels.

* * * * *